United States Patent
Peterson et al.

(10) Patent No.: US 10,987,116 B2
(45) Date of Patent: Apr. 27, 2021

(54) ADJUSTABLE DRILL GUIDES AND RELATED METHODS

(71) Applicant: Medos International Sarl, Le Locle (CH)

(72) Inventors: Joseph Peterson, South Dartmouth, MA (US); Felix Aschmann, Basel (CH); John Riley Hawkins, Cumberland, RI (US)

(73) Assignee: Medos International Sarl, Le Locle (CH)

( * ) Notice: Subject to any disclaimer, the term of this patent is extended or adjusted under 35 U.S.C. 154(b) by 258 days.

(21) Appl. No.: 15/843,617

(22) Filed: Dec. 15, 2017

(65) Prior Publication Data

US 2019/0183516 A1 Jun. 20, 2019

(51) Int. Cl.
*A61B 17/58* (2006.01)
*A61B 17/60* (2006.01)
(Continued)

(52) U.S. Cl.
CPC .......... *A61B 17/1757* (2013.01); *A61B 17/17* (2013.01); *A61B 34/20* (2016.02);
(Continued)

(58) Field of Classification Search
CPC combination set(s) only.
See application file for complete search history.

(56) References Cited

U.S. PATENT DOCUMENTS

| 4,004,581 A | 1/1977 | Heimke et al. |
| 5,234,434 A | 8/1993 | Goble et al. |

(Continued)

FOREIGN PATENT DOCUMENTS

WO 2008/100253 A1 8/2008

OTHER PUBLICATIONS

[NoAuthorListed] DePuy Synthes C1/C2 Access System Surgical Technique guide, 2016.
(Continued)

*Primary Examiner* — Sameh R Boles
(74) *Attorney, Agent, or Firm* — Nutter McClennen & Fish LLP

(57) ABSTRACT

Adjustable drill guides and related methods are disclosed herein. An exemplary drill guide can include an adjustment mechanism that allows for precise incremental adjustment of the drill guide's depth setting while securely maintaining the device at a fixed setting between adjustments. The adjustment mechanism can improve the safety and security of the drill guide, for example by limiting adjustment only to those situations where it is specifically intended by the user, thereby reducing or eliminating the risk of inadvertent depth adjustment. In some embodiments, a drill guide can include high visibility, easy-to-read depth indications while maintaining a slender profile and without shifting the user's eye gaze, for example by employing a multi-surface moving scale having a text height that is at least twice the adjustment increment. Handles, protection sleeves, navigation adapters, and various other accessories that can be used with or without a drill guide are also disclosed herein.

20 Claims, 25 Drawing Sheets

(51) Int. Cl.

| | | |
|---|---|---|
| *A61F 2/00* | (2006.01) | |
| *A61B 17/17* | (2006.01) | |
| *A61B 34/20* | (2016.01) | |
| *A61B 17/02* | (2006.01) | |
| *A61B 17/00* | (2006.01) | |
| *A61B 90/00* | (2016.01) | |
| *A61B 17/70* | (2006.01) | |
| *A61B 17/88* | (2006.01) | |

(52) U.S. Cl.
CPC ......... *A61B 17/025* (2013.01); *A61B 17/7082* (2013.01); *A61B 17/8875* (2013.01); *A61B 2017/00473* (2013.01); *A61B 2017/00991* (2013.01); *A61B 2017/0256* (2013.01); *A61B 2034/2055* (2016.02); *A61B 2090/034* (2016.02); *A61B 2090/062* (2016.02); *A61B 2090/3983* (2016.02)

(56) References Cited

U.S. PATENT DOCUMENTS

| | | |
|---|---|---|
| 5,484,446 A | 1/1996 | Burke et al. |
| 5,669,915 A | 9/1997 | Caspar et al. |
| 5,810,828 A | 9/1998 | Lightman et al. |
| 5,885,298 A | 3/1999 | Herrington et al. |
| 6,110,178 A | 8/2000 | Zech et al. |
| 6,277,121 B1 | 8/2001 | Burkinshaw et al. |
| 6,514,258 B1 | 2/2003 | Brown et al. |
| 6,739,872 B1 | 5/2004 | Turri |
| 6,866,667 B2 | 3/2005 | Wood et al. |
| 6,929,647 B2 | 8/2005 | Cohen |
| 7,314,048 B2 | 1/2008 | Couture et al. |
| 7,491,203 B2 | 2/2009 | Harris, Jr. et al. |
| 7,771,143 B2 | 8/2010 | Bharadwaj et al. |
| 8,480,682 B2 | 7/2013 | Howlett et al. |
| 9,155,545 B2 | 10/2015 | Prescott |
| 9,277,926 B2 | 3/2016 | Xu et al. |
| 9,393,039 B2 | 7/2016 | Lechner et al. |
| 9,526,548 B2 | 12/2016 | Asfora |
| 9,572,589 B2 | 2/2017 | Knape et al. |
| 2002/0193780 A1 | 12/2002 | Karray et al. |
| 2003/0233098 A1 | 12/2003 | Markworth |
| 2006/0264955 A1 | 11/2006 | Abdelgany |
| 2009/0228047 A1 | 9/2009 | Derouet et al. |
| 2010/0262200 A1 | 10/2010 | Ray, III et al. |
| 2012/0123417 A1 | 5/2012 | Smith |
| 2014/0155905 A1* | 6/2014 | Keiser ............ A61B 17/17 606/96 |
| 2014/0276880 A1 | 9/2014 | Li |
| 2014/0343553 A1 | 11/2014 | Ford et al. |
| 2015/0164518 A1 | 6/2015 | Jinton et al. |
| 2015/0343553 A1 | 12/2015 | Mol et al. |
| 2016/0074652 A1 | 3/2016 | Hamilton |
| 2016/0324552 A1 | 11/2016 | Baker et al. |
| 2017/0071588 A1 | 3/2017 | Choi et al. |
| 2017/0209154 A1 | 7/2017 | Krause et al. |
| 2018/0344301 A1 | 12/2018 | Wehrli et al. |

OTHER PUBLICATIONS

International Search Report and Written Opinion for Application No. PCT/SU18/65504, dated Jun. 18, 2019 (14 pages).

* cited by examiner

FIG. 1C
FIG. 1D
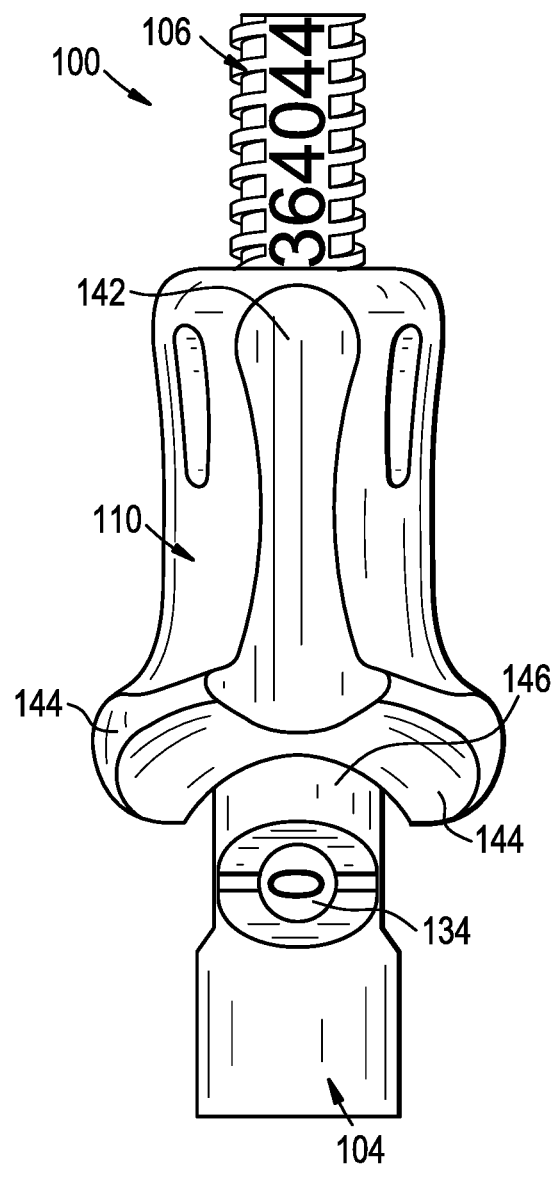
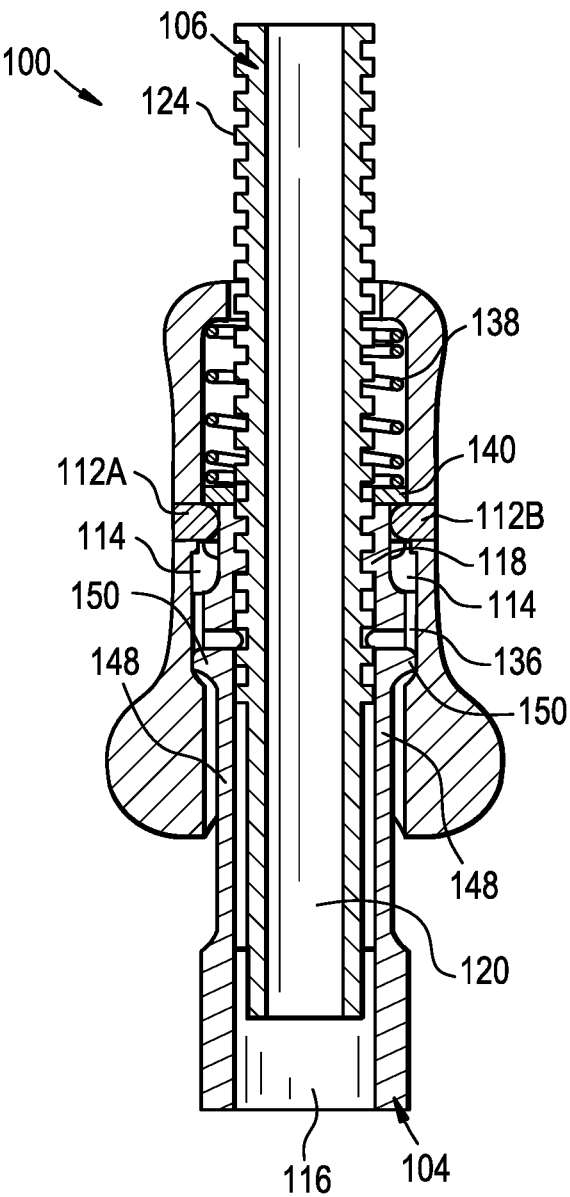

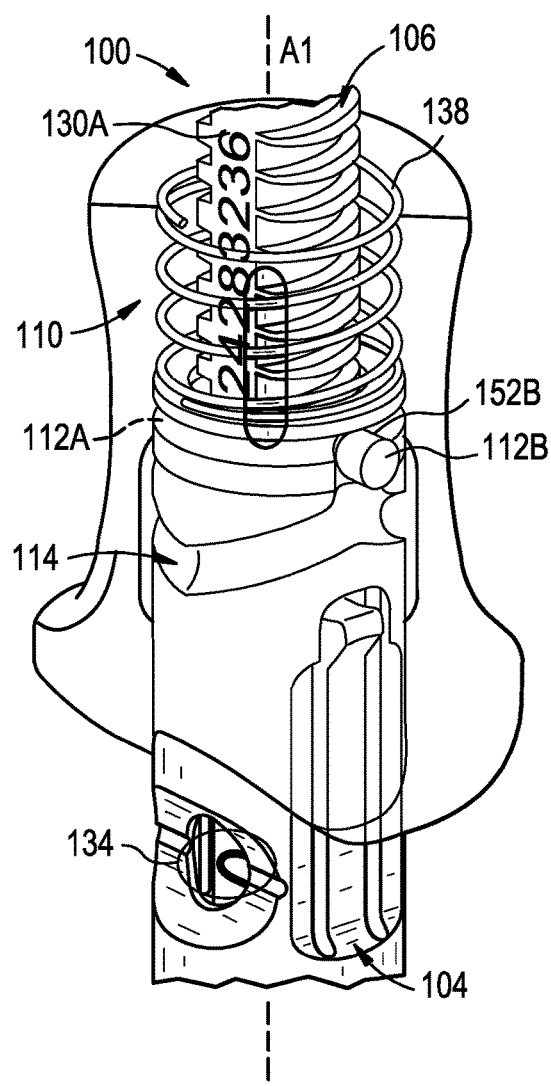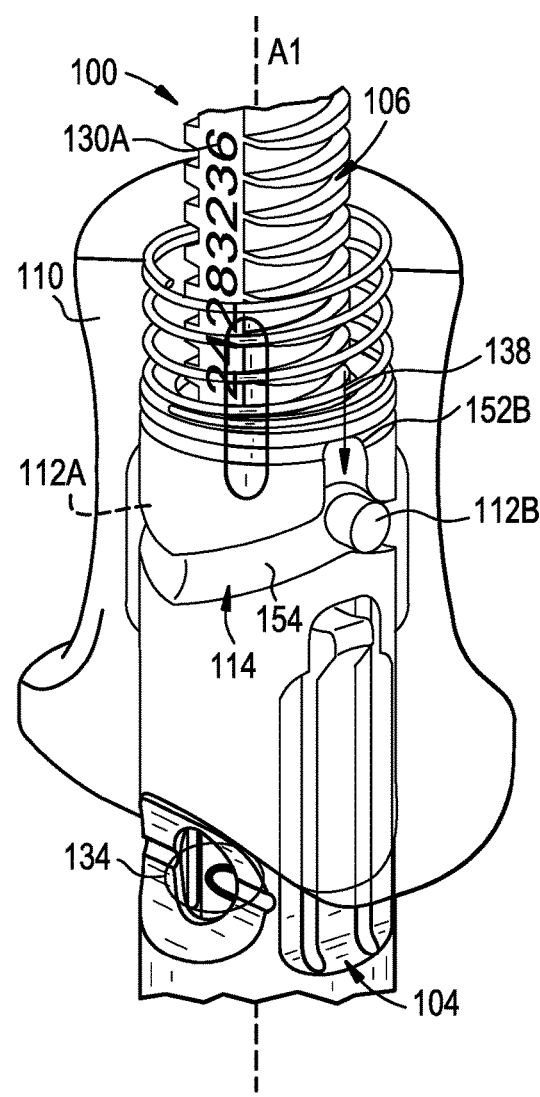

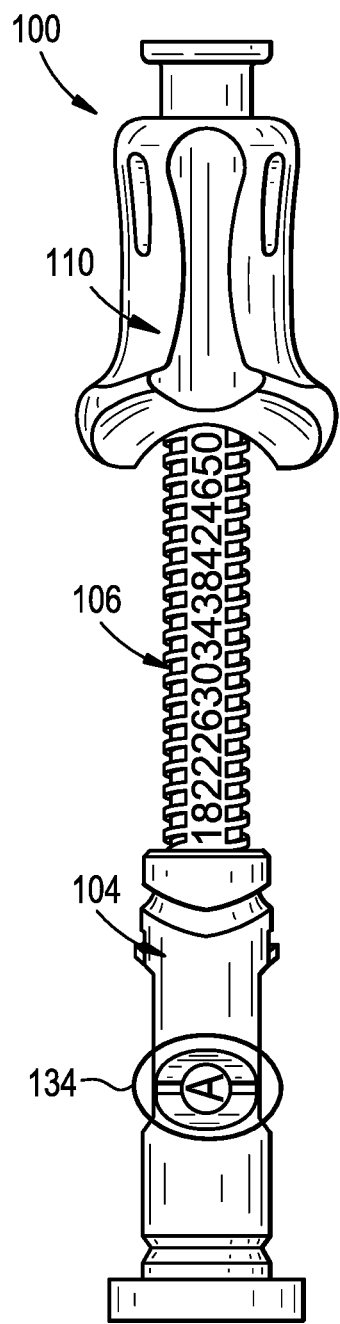
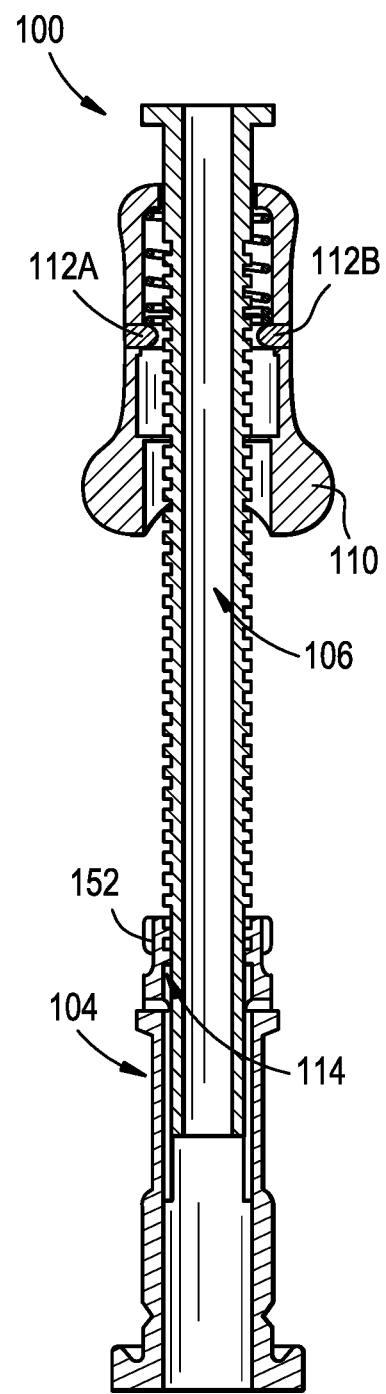

FIG. 3E
FIG. 3F
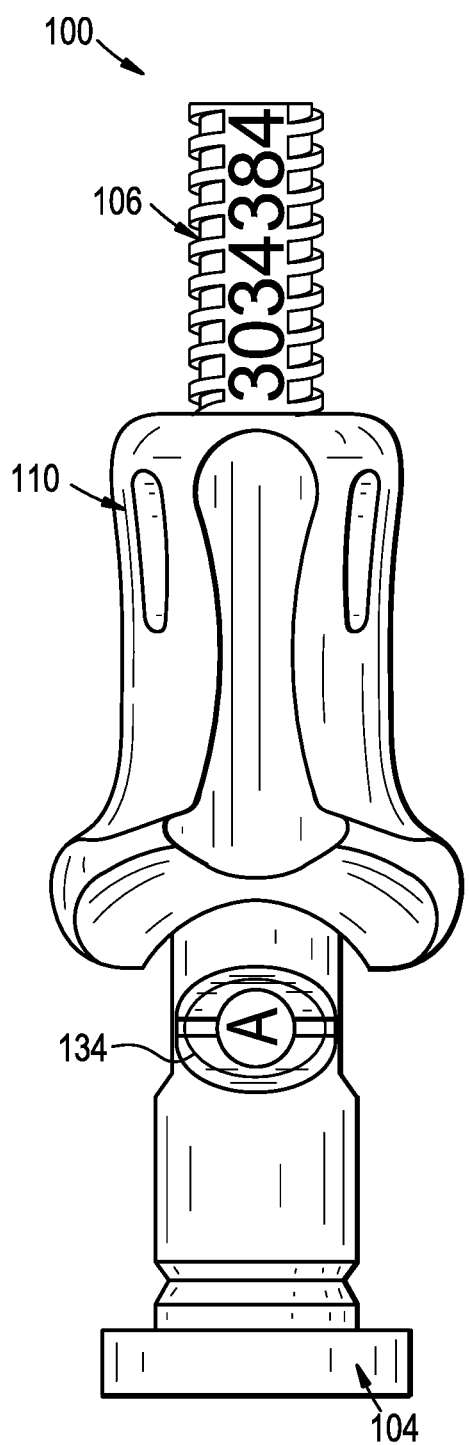
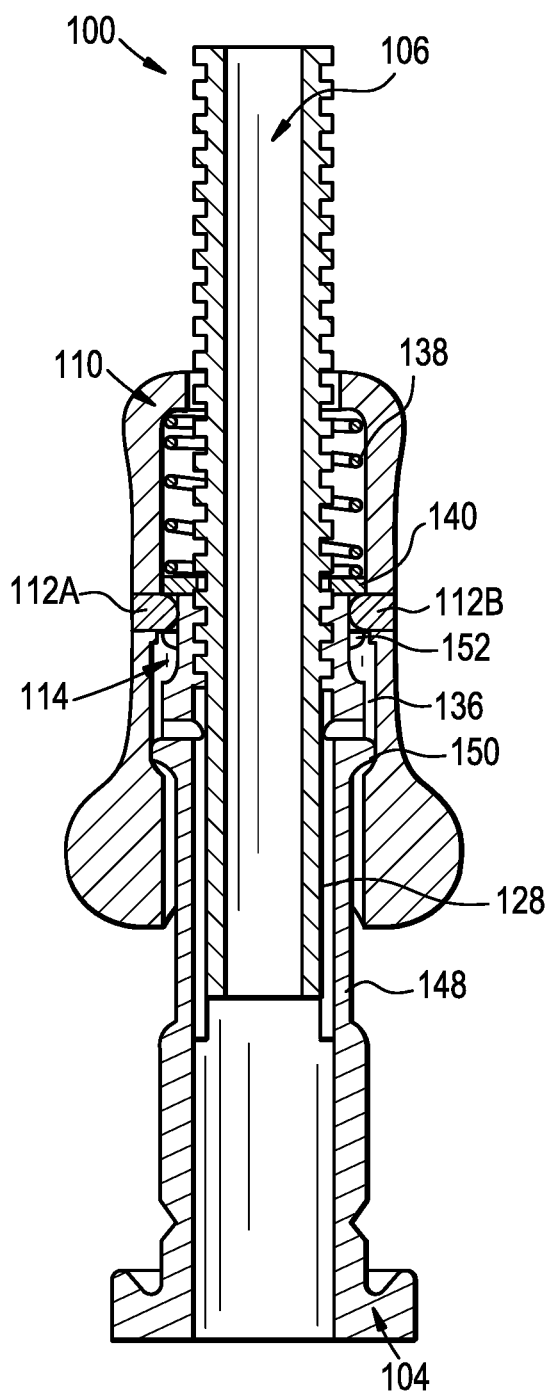

FIG. 3G
FIG. 3H
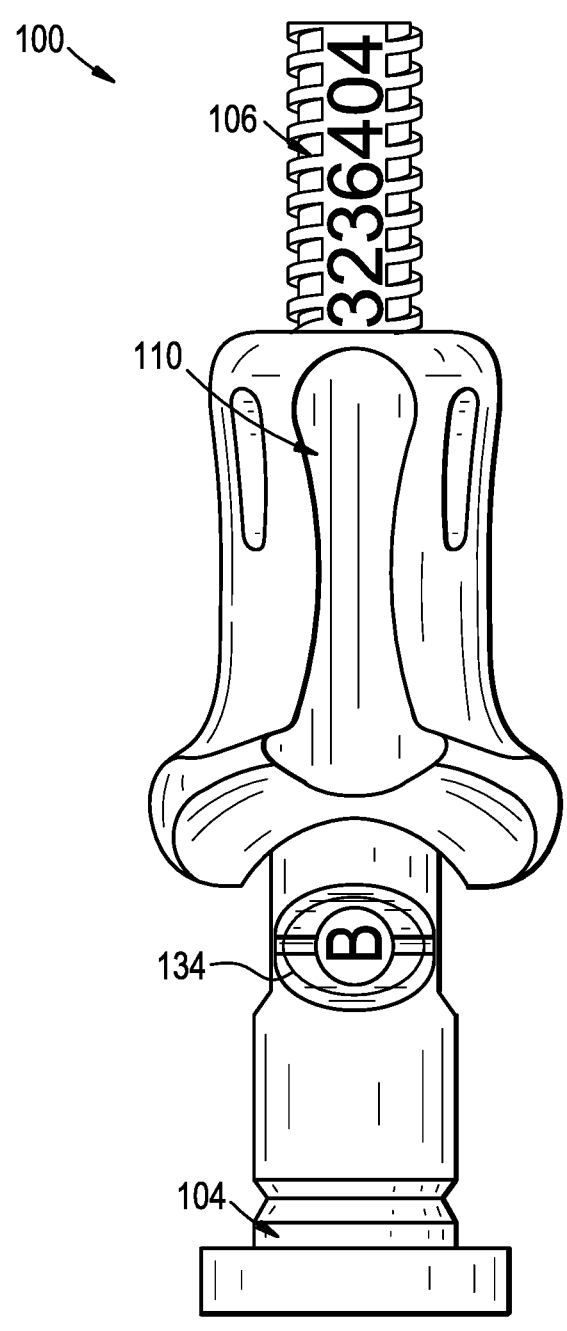
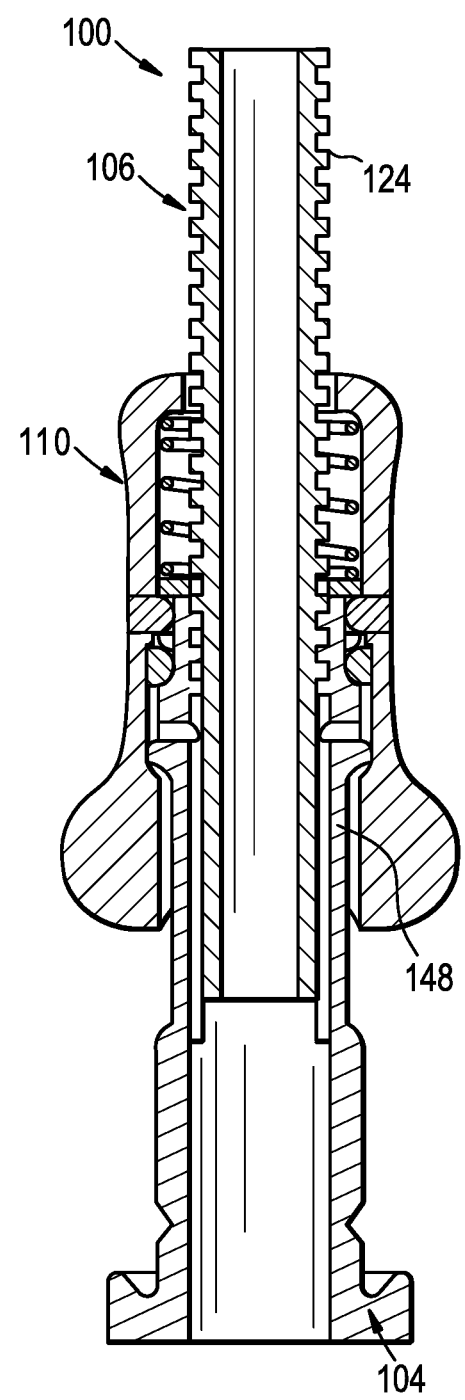

FIG. 3I
FIG. 3J
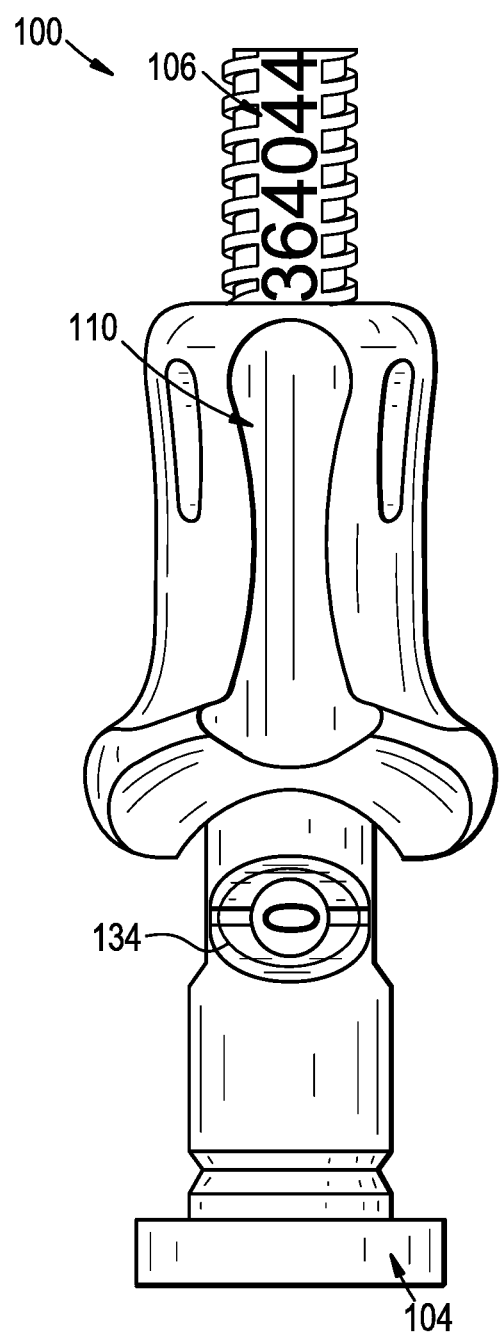
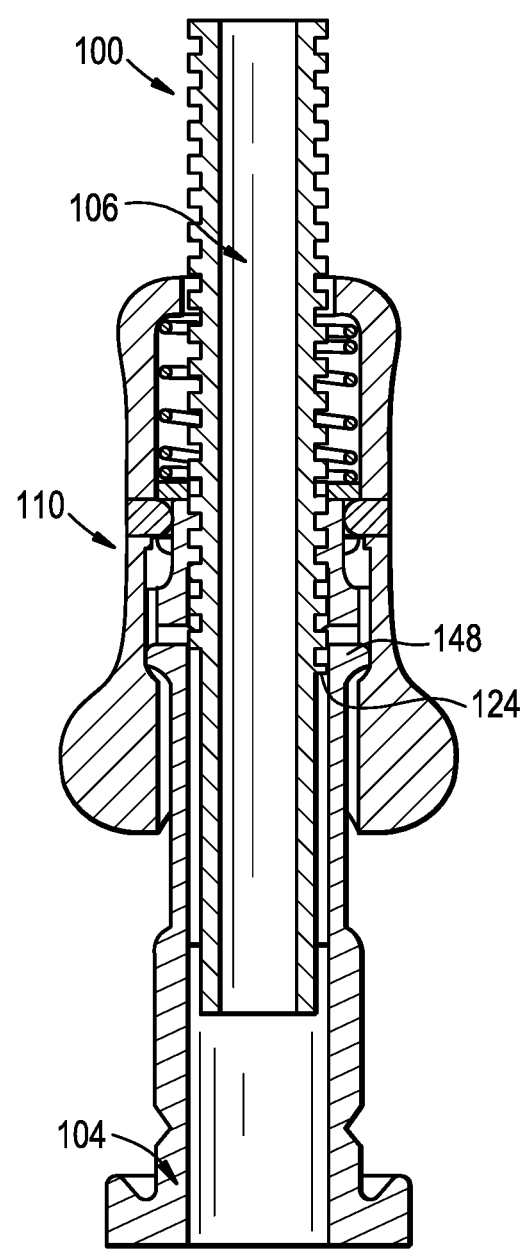

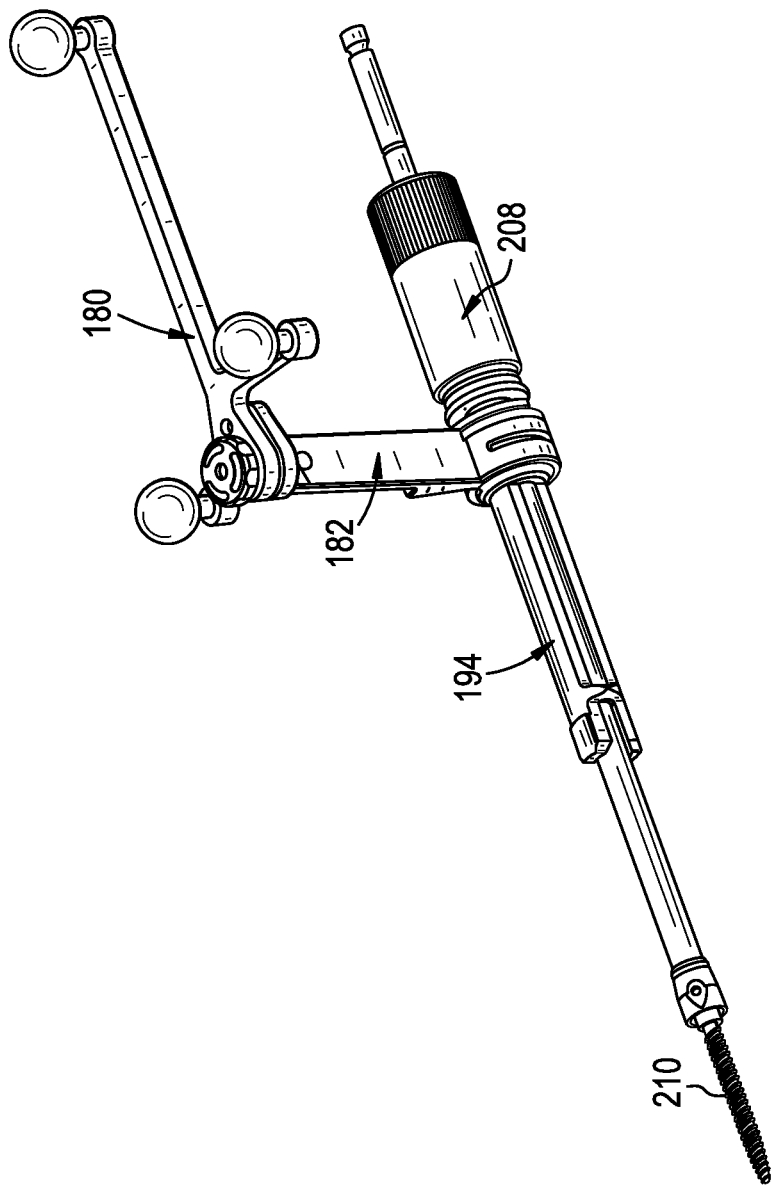

ADJUSTABLE DRILL GUIDES AND RELATED METHODS

FIELD

Adjustable drill guides and related methods are disclosed herein.

BACKGROUND

There are a number of surgical procedures in which it is necessary or desirable to drill a hole. For example, holes are often drilled in bone using a rotary drill bit to prepare the bone to receive a screw or other bone anchor. A number of drill guides have been developed to guide the drill bit along the proper axis, and/or to set the depth to which the drill bit penetrates the bone. Conventional drill guides generally include a handle having an adjustable length sleeve attached thereto. When used in conjunction with a drill bit having a fixed stop, the length of the sleeve can control the depth to which the drill penetrates the bone (and the depth of the consequent hole).

Drill guides are often used in spinal surgery, such as when applying posterior cervical fixation. Drilling in and around the spine can be very risky due to the presence of nerves, vasculature, and other sensitive anatomical structures in close proximity to the drill bit. One must be extremely precise with the drill location, orientation, and depth so as not to harm the patient. In an exemplary procedure, a drill guide or sleeve is placed on a pedicle entry point and a drill is inserted through the proximal opening of the guide. The drill includes a stop that contacts the proximal end of the guide to limit penetration depth into the underlying bone.

Conventional drill guides often use a ratchet mechanism for setting the depth. While such mechanisms can provide fast depth adjustment and easy assembly, there may be a risk that the ratchet mechanism disengages during the procedure, resulting in inadvertent depth adjustment and possibly catastrophic over-insertion of the drill.

Conventional drill guides also have depth scale labels that can be too small and difficult for the user to read. Generally, the text height of the labels is limited to the associated depth increment or implant increment. The typical implant increment for drilled screw holes in spinal surgery is only 2 mm (0.079 inches). The American National Standard on Human factors engineering, ANSI/AAMI HE75:2009, however, recommends text of 0.125 inches or larger for effective transmission of information. The use of 2 mm text on conventional drill guides is a frequent surgeon complaint and may lead to incorrect depth settings if the label is read incorrectly. Attempts to increase the size of the label text have resulted in a corresponding increase in the size or diameter of the drill guide. Increased drill guide size or diameter can be a drawback in many situations. For example, when used in minimally invasive surgical wounds which have a limited opening size, increasing the instrument diameter can occlude the user's view of surrounding tissues or otherwise impede the procedure. Other attempts to increase the size of the label text incorporate techniques to move the user's eye gaze to another location that can accommodate oversized text. This technique also increases the size of the drill guide, and shifting the user's eye gaze can decrease the usability of the instrument.

In view of these and other challenges, there is a continual need for improved drill guides and related methods.

SUMMARY

Adjustable drill guides and related methods are disclosed herein. An exemplary drill guide can include an adjustment mechanism that allows for precise incremental adjustment of the drill guide's depth setting while securely maintaining the device at a fixed setting between adjustments. The adjustment mechanism can improve the safety and security of the drill guide, for example by limiting adjustment only to those situations where it is specifically intended by the user, thereby reducing or eliminating the risk of inadvertent depth adjustment. In some embodiments, a drill guide can include high visibility, easy-to-read depth indications while maintaining a slender profile and without shifting the user's eye gaze, for example by employing a multi-surface moving scale having a text height that is at least twice the adjustment increment. Handles, protection sleeves, navigation adapters, and various other accessories that can be used with or without a drill guide are also disclosed herein.

In some embodiments, an adjustable length guide device can include a body having a proximal end, a distal end, and a central longitudinal axis extending between the proximal and distal ends; a stem movably coupled to the body, the body and the stem together defining an adjustable length guide lumen; and an adjustment mechanism that controls movement of the stem relative to the body to incrementally adjust the length of the guide lumen; wherein the adjustment mechanism comprises a knob having at least one pin received within a groove formed in an outer surface of the body; wherein the at least one pin is positionable in: (i) a locking region of the groove to prevent adjustment of the length of the guide lumen; and (ii) an adjustment region of the groove to allow adjustment of the length of the guide lumen.

Positioning the at least one pin in the locking region of the groove can prevent the knob and the stem from rotating relative to body about the central longitudinal axis while allowing the knob to translate longitudinally relative to body. Positioning the at least one pin in the adjustment region of the groove can allow the knob and the stem to rotate relative to the body about the central longitudinal axis. The stem can be threadably engaged with the body. The knob can be rotationally fixed relative to the stem such that rotation of the knob relative to the body adjusts the length of the guide lumen. The knob can be movable relative to the body in an adjustment cycle in which the knob (i) translates distally relative to the body by a first distance, (ii) rotates relative to the body by a first rotational amount, and (iii) returns proximally relative to the body by the first distance, the adjustment cycle being effective to adjust the length of the guide lumen by one increment. The adjustment cycle can include moving the at least one pin out of the locking region of the groove, along the adjustment region of the groove, and back into the locking region of the groove. The first rotational amount can be less than 360 degrees. The first rotational amount can be 180 degrees. Rotating the knob relative to the body by the first rotational amount can translate the knob distally relative to the body by a second amount and return the knob proximally relative to the body by the second amount. The locking region of the groove can include first and second diametrically opposed longitudinal sections of the groove oriented parallel to the longitudinal axis of the body. The adjustment region of the groove can include first and second diametrically opposed circumferential sections of the groove connecting the first and second longitudinal sections. Each of the circumferential sections can be chevron-shaped. Each of the circumferential sections can include a quarter turn helical down thread and a quarter turn helical up thread. The knob can be biased proximally relative to the body to urge the at least one pin towards the locking region of the groove.

The device can include a handle selectively attachable to the body. The handle can include an inner locking shaft rotatable relative to an outer shaft of the handle between a locked position, in which a distal tip of the locking shaft engages the body to lock the handle to the body, and an unlocked position in which the distal tip of the locking shaft does not engage the body. The distal tip can include a slash-cut portion that is aligned with a groove in the body in the unlocked position and a non-cut portion that is disposed in the groove in the body in the locked position.

In some embodiments, a method of adjusting a depth setting of a guide device can include moving a stem of the device relative to a body of the device to adjust a length of a guide lumen defined by the stem and the body, wherein moving the stem includes: translating a knob distally along the body by a first distance to move at least one pin along a locking portion of a groove formed in the body and into an adjustment portion of the groove; rotating the knob relative to the body to move the at least one pin through the adjustment portion of the groove, wherein rotating the knob causes the stem to rotate relative to the body to adjust the length of the guide lumen; and translating the knob proximally along the body by the first distance to move the at least one pin out of the adjustment portion of the groove and back into the locking portion of the groove.

Moving the stem relative to the body can include threading the stem into or out of the body. Rotating the knob relative to the body can cause the knob to translate distally relative to the body by a second amount and to return proximally relative to the body by the second amount. Rotating the knob relative to the body can include rotating the knob 180 degrees about a central longitudinal axis of the body. The at least one pin can include first and second pins. Rotating the knob relative to the body can include moving the first pin from a first vertical section of the locking portion to a second opposite vertical section of the locking portion and moving the second pin from the second vertical section to the first vertical section.

In some embodiments, an adjustable length guide device can include a body having a proximal end, a distal end, and a central longitudinal axis extending between the proximal and distal ends; a stem movably coupled to the body, the body and the stem together defining an adjustable length guide lumen, the stem including a measurement scale; and an adjustment mechanism that controls movement of the stem relative to the body to incrementally adjust the length of the guide lumen; wherein the measurement scale is spread across first and second separate surfaces of the stem.

The first and second surfaces can be movable with respect to the body to selectively position one of said surfaces in alignment with a viewing window of the body. The first and second surfaces can be diametrically opposed from one another. The stem can include an external thread. The first and second surfaces can be opposed planar side surfaces that interrupt the thread. Rotating the stem relative to the body can adjust the length of the guide lumen and can select which of the first and second surfaces is aligned with a viewing window of the body. The scale can include a plurality of numerical markings, each marking having a text height and a text width. The stem can include an external thread and the lead of the thread can be twice the text height of the markings. The markings can be divided in numerically-alternating fashion across the first and second surfaces. The text height of the markings can be greater than an adjustment increment of the device. The text height of the markings can be at least twice an adjustment increment of the device. The text width of the markings can be at least twice an adjustment increment of the device. The text height of the markings can be at least 3.5 mm. The text width of the markings can be at least 3.5 mm. All of the markings on the first surface can be aligned along a common axis. A lateral dimension of the scale can be equal or substantially equal to the text height of a single marking.

In some embodiments, a method of adjusting a depth setting of a guide device can include moving a stem of the device relative to a body of the device to adjust a length of a guide lumen defined by the stem and the body; wherein the stem includes a measurement scale spread across first and second separate surfaces of the stem; wherein moving the stem relative to the body is effective to select which of the first and second surfaces is aligned with a viewing area of the device.

Moving the stem can include rotating the stem about a central longitudinal axis of the body to advance or retract the stem relative to the body via a threaded engagement between the stem and the body. The viewing area can include a viewing window formed in the body. The first and second surfaces can be diametrically opposed planar side surfaces of the stem.

In some embodiments, a protection sleeve can include an elongate body having a proximal end, a distal end, a central longitudinal axis extending between the proximal and distal ends, an outer sidewall, and an inner lumen; and an opening in the outer side wall, the opening extending an entire length of the body and being configured to receive a protrusion of an instrument inserted through the body to guide movement of the instrument.

The sleeve can include an arm that extends radially outward from the body, the arm being configured to attach a modular handle to the sleeve. The sleeve can include a spring tab configured to clip into engagement with an instrument inserted through the lumen of the sleeve.

In some embodiments, a navigation adapter can include a body defining a lumen configured to receive an instrument or implant therethrough; a mating interface for attaching the body to a navigation array; a button movable relative to the body to engage or disengage from an instrument inserted through the body; and a lug that protrudes radially-outward from the body.

In some embodiments, a surgical method can include adjusting a depth setting of a drill guide to a desired drilling depth; positioning a distal tip of the drill guide in contact with a bone entry point on a bone of a patient; aligning a longitudinal axis of the drill guide with a desired drilling trajectory; inserting a drill through the drill guide; drilling a hole in the bone through the bone entry point, along the desired drilling trajectory, and to the desired drilling depth; positioning a navigation adapter along the desired drilling trajectory; inserting an anchor driver and a bone anchor through the navigation adapter; and using the anchor driver, driving the bone anchor into the hole in the bone, a navigation array of the navigation adapter being used during said driving to provide navigation feedback.

The method can include inserting a bone tap through the navigation adapter and tapping the hole formed in the bone using the bone tap. The drill guide and the navigation adapter can be inserted through a protection sleeve. The method can include engaging a spring tab of the protection sleeve with a groove formed in the drill guide to prevent longitudinal movement of the drill guide relative to the protection sleeve during said drilling. The method can include advancing the navigation adapter and the anchor driver distally relative to the protection sleeve as the bone anchor is driven into the bone. A lug of the navigation adapter can slide within a track of the protection sleeve to guide advancement of the navigation adapter. The track of the protection sleeve can include a longitudinal gap in a sidewall of the protection sleeve. The method can include using a navigation array attached to the drill guide to provide navigation feedback during positioning of the drill guide. The desired trajectory can extend through C1 and C2 vertebrae of the patient.

BRIEF DESCRIPTION OF THE DRAWINGS

FIG. 1C is a detail side view of the drill guide of FIG. 1A;
FIG. 1D is a sectional side view of the drill guide of FIG. 1A;
FIGS. 2A-2E schematically illustrate a depth adjustment sequence of the drill guide of FIG. 1A;
FIGS. 3A-3J schematically illustrate an assembly sequence of the drill guide of FIG. 1A;
FIG. 8F is a perspective view of the navigation adapter of FIG. 8A guiding a driver instrument and bone anchor without use of a protection sleeve.

DETAILED DESCRIPTION

Figure 1A:
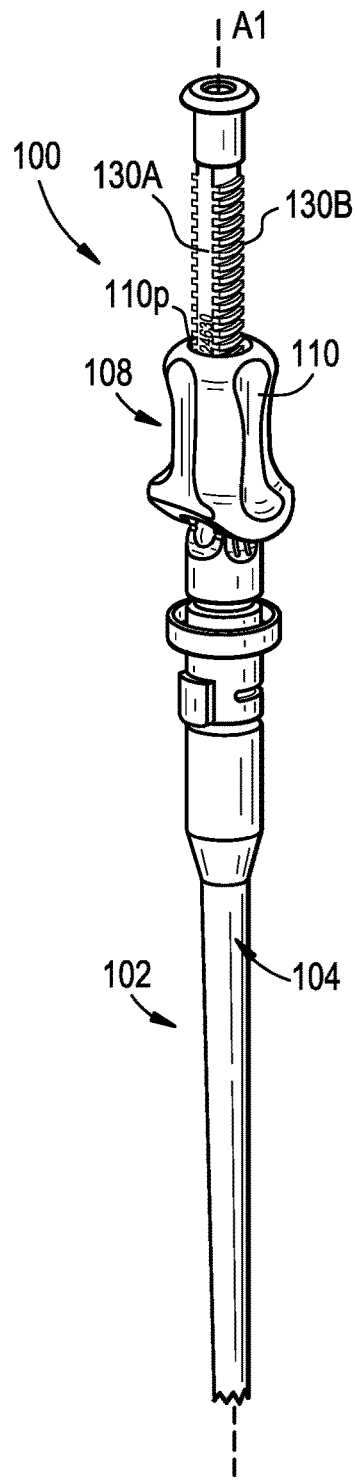
FIG. 1A is a perspective view of a drill guide.
Figure 1B:
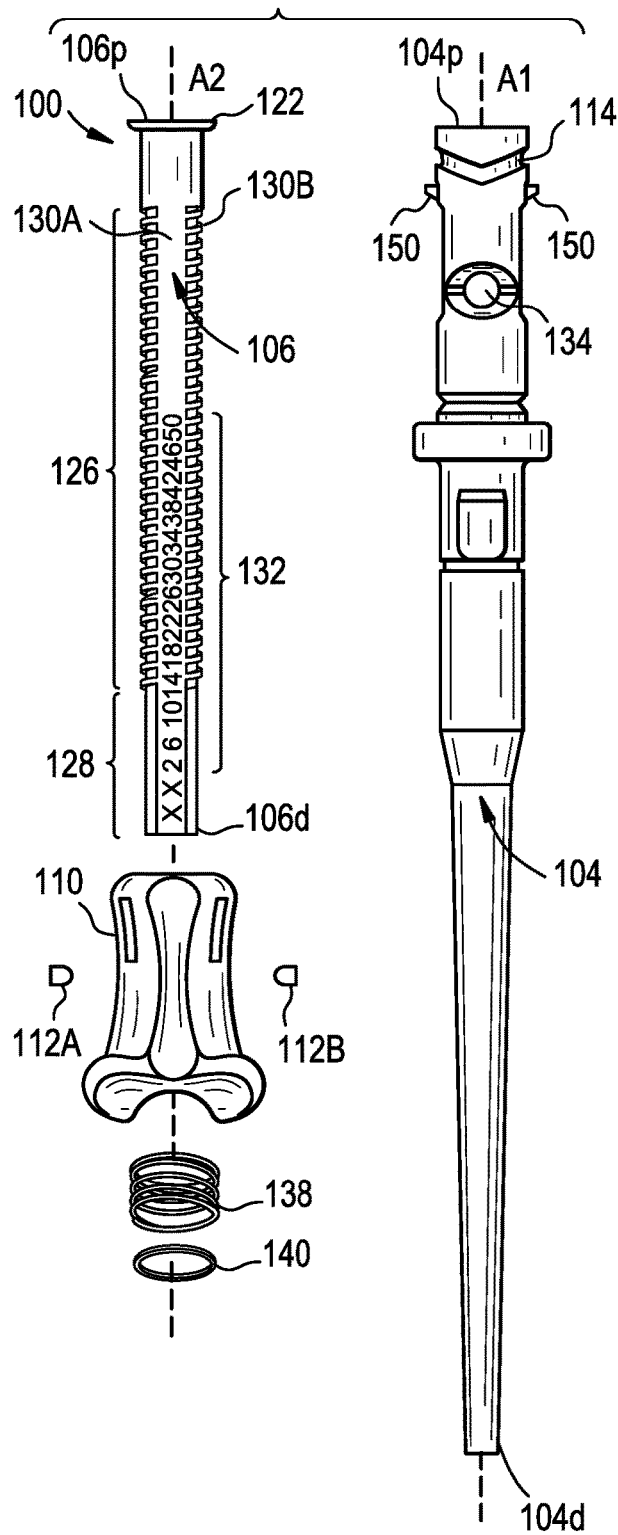
FIG. 1B is an exploded side view of the drill guide of FIG. 1A.

Adjustable drill guides and related methods are disclosed herein. An exemplary drill guide can include an adjustment mechanism that allows for precise incremental adjustment of the drill guide's depth setting while securely maintaining the device at a fixed setting between adjustments. The adjustment mechanism can improve the safety and security of the drill guide, for example by limiting adjustment only to those situations where it is specifically intended by the user, thereby reducing or eliminating the risk of inadvertent depth adjustment. In some embodiments, a drill guide can include high visibility, easy-to-read depth indications while maintaining a slender profile and without shifting the user's eye gaze, for example by employing a multi-surface moving scale having a text height that is at least twice the adjustment increment. Handles, protection sleeves, navigation adapters, and various other accessories that can be used with or without a drill guide are also disclosed herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1A-1D illustrate an exemplary drill guide 100. The guide 100 can include a sleeve 102 defined by a main body 104 and a scale or stem 106. The stem 106 can be configured to move relative to the body 104 to adjust the effective length of the sleeve 102 and thus the maximum depth setting of the guide 100. The stem 106 can be threaded into or onto the body 104, such that the depth setting can be adjusted by rotating the stem relative to the body.

This relative rotation between the body 104 and the stem 106 can be controlled by an adjustment mechanism 108. The adjustment mechanism 108 can be configured such that a compound user input movement is required to adjust the depth setting. For example, the adjustment mechanism 108 can be configured such that a combination and/or sequence of longitudinal translation and axial rotation is required to rotate the stem 106 relative to the body 104. This can advantageously limit adjustment of the guide 100 to only those times when adjustment is specifically intended by the user, preventing inadvertent depth adjustment.

The adjustment mechanism 108 can be configured to limit adjustment of the depth to one predetermined increment for each user input movement. For example, the adjustment mechanism 108 can be configured to automatically return to a locked or safety configuration after each incremental adjustment of depth. This can provide enhanced user confidence that a depth change occurred, allow the user to easily achieve the desired depth change by providing a corresponding number of input movements, and prevent the guide 100 from being left in a state of partial or incomplete incremental adjustment.

The adjustment mechanism 108 can include a knob 110. The knob 110 can be configured to limit the stem 106 and the body 104 to certain relative movements, e.g., via interaction between one or more guide pins or protrusions 112 of the knob and one or more guide slots or grooves 114 of the body. The guide pins 112 can be positioned within a locking region of the groove 114 to prevent rotation between the stem 106 and the body 104 and thereby maintain a fixed depth setting. To adjust the depth setting, the guide pins 112 can be moved to an adjustment region of the groove 114 in which some relative rotation between the stem 106 and the body 104 is permitted. The adjustment region can be configured to only allow depth adjustment by one increment at a time, e.g., by automatically returning the guide pins 112 to the locking region of the groove 114 between each depth increment. In the illustrated arrangement, the depth is adjusted by (1) sliding the knob 110 distally along the body 104 to move the guide pins 112 out of the locking region of the groove 114, (2) rotating the knob relative to the body to rotate the stem 106 within the body and advance or retract the stem relative to the body via a threaded engagement therebetween, and (3) returning the knob proximally along the body to move the guide pins back into the locking region of the groove. The above steps can be repeated as many times as needed to adjust the depth to the desired setting. The depth setting can be increased by rotating the knob 110 in a first direction relative to the body 104 and can be decreased by rotating the knob in a second, opposite direction relative to the body. It will be appreciated that the location of the pins 112 and the groove 114 can be reversed or modified from what is shown, e.g., such that a male feature or pin is formed on the body 104 and a female feature or groove is formed in the knob 110. While pins 112 are shown, the protrusion can be various other structures instead or in addition, such as tabs, partial thread portions, or ball-type features.

Once the desired depth setting is reached, a drill bit can be advanced through a lumen defined by the sleeve 102 and into target tissue disposed adjacent the distal end of the guide 100. As the drill bit is advanced, a stop on the drill bit or on the drill can contact the proximal end of the stem 106 to prevent the drill bit from exceeding the maximum drilling depth. While reference is generally made herein to guiding a drill bit, it will be appreciated that the guide 100 can be used with any of a variety of instruments or other objects, such as a bone tap, guidewire, or needle, and is not limited to use with drills or drill bits.

The drill guide 100 can include a multi-surface depth scale. This can allow the depth labels to be divided across the multiple surfaces, thereby providing more area for the labels such that the text size of the labels can be made larger without increasing the overall diameter or profile of the guide 100. The multiple surfaces can be selectively aligned with a stationary viewing area or window of the guide 100 in concert with the depth adjustment. Accordingly, the user's gaze need not be shifted away from the guide 100 or move to another portion of the guide.

As shown in FIGS. 1A-1D, the body 104 can include a proximal end 104p, a distal end 104d, and a central longitudinal axis A1 extending therebetween. The body 104 can define a central lumen 116 in which at least a portion of the stem 106 can be received and through which a drill bit or other object can be inserted. At least a portion of the central lumen 116 can be threaded. For example, as shown, a section of the lumen 116 adjacent the proximal end 104p of the body 104 can define an interior thread 118. The thread 118 of the body 104 can mate with a thread of the stem 106 to adjust the longitudinal position of the stem 106 relative to the body 104.

The stem 106 can include a proximal end 106p, a distal end 106d, and a central longitudinal axis A2 extending therebetween. The stem 106 can define a central lumen 120 through which a drill bit or other object can be inserted. When assembled to the body 104, the central lumen 120 of the stem 106 can be in communication with the central lumen 116 of the body. The body 104 and the stem 106 can be coaxially assembled to one another, e.g., such that the central longitudinal axes A1, A2 are coincident with one another. The proximal end 106p of the stem 106 can include a radial flange, shoulder, or other stop surface 122. In use, the degree to which a drill or other object can be inserted through the guide 100 can be limited by contact between a stop surface of the inserted object and the stop surface 122 of the stem 106.

At least a portion of the outer surface of the stem 106 can be threaded. The thread 124 of the stem 106 can mate with the internal thread 118 of the body 104 to adjust the longitudinal position of the stem relative to the body. The stem 106 can include a proximal threaded portion 126 and a distal unthreaded portion 128. As described further below, the longitudinal lengths of the threaded and unthreaded portions 126, 128 can cooperate with retention features of the guide 100 to prevent disassembly in certain device states. The thread 124 of the stem can be a helical thread.

The lead of the thread 124 on the stem 106 (and of the counterpart thread 118 of the body 104), e.g., the axial distance the stem moves in one revolution, can be selected according to the desired depth adjustment increment. Matching the depth adjustment increment of the guide 100 to the length increment of a bone anchor set with which the guide is to be used can advantageously make the combined system easier to use and more intuitive for the user. Thus, when the guide 100 is to be used with a bone anchor set provided in 2 mm anchor length increments, the depth adjustment increment of the guide 100 can be 2 mm. As described further below, a 180 degree rotation of the stem 106 relative to the body 104 can be effective to adjust the depth setting of the guide 100 by one increment. In such cases, the thread lead of the stem 106 can be set to twice the depth adjustment increment so that each 180 degree rotation adjusts the depth setting by one increment. In the example above with a 2 mm depth increment, the thread lead of the stem 106 can be 4 mm. Accordingly, each 180 degree rotation of the stem 106 relative to the body 104 can adjust the depth setting by 2 mm, corresponding to the bone anchor increment of the set.

The stem 106 can have a generally cylindrical outer surface. The stem 106 can include one or more flats or planar outer surfaces. The flats of the stem 106 can be aligned with corresponding flats of the adjustment knob 110 to restrict relative axial rotation between the stem and the knob. Accordingly, rotation of the knob 110 about the axis A1 can be effective to rotate the stem 106 about the axis A1 and vice versa. Further, locking rotation of the knob 110 about the axis A1 can be effective to likewise lock rotation of the stem 106 about the axis A1. The flats of the stem 106 can extend along a portion of the length of the stem or along an entirety thereof. In the illustrated arrangement, the flats of the stem 106 extend along an entire length of the stem, except for the proximal stop shoulder 122. The flats of the stem 106 can be defined by diametrically-opposed planar outer side surfaces 130A, 130B of the stem as shown. The flats can interrupt the thread 124 of the threaded portion 126 of the stem 106, such that the thread is discontinuous about the circumference or outer perimeter of the stem. While two flats are shown, the stem 106 can include any number of flats, e.g., one or more.

The stem 106 can include a depth scale 132 including a plurality of depth markings or labels. The depth scale 132 can be printed, engraved, or otherwise formed on the stem 106. The depth scale 132 can be divided or spread across multiple surfaces of the stem 106. This can advantageously provide increased area for the depth markings, thereby allowing larger, more-visible markings to be used. For example, the depth scale 132 can be spread across the first and second opposed side surfaces 130A, 130B of the stem 106. The stem 106 can be configured to rotate relative to the body 104, and therefore each of the surfaces 130A, 130B can be selectively aligned with a fixed viewing window 134 of the body 104. This can allow the user's eye gaze to remain on one fixed location (e.g., the viewing window 134) while still being able to view depth markings formed on multiple surfaces.

As noted above and described in further detail below, a 180 degree rotation of the stem 106 relative to the body 104 can be effective to adjust the depth setting of the guide 100 by one increment. Accordingly, the surface 130A or 130B that is aligned with the viewing window 134 can alternate with each successive increment. In such arrangements, the depth labels can be divided in numerically-alternating fashion across the first and second surfaces 130A, 130B. For example, in the illustrated embodiment in which the depth setting increment is 2 mm, markings are provided for each 2 mm depth increment, with the markings for 2, 6, 10, 14, 18, 22, 26, 30, 34, 38, 42, 46, 50, etc. mm being formed on the first surface 130A and the markings for 0, 4, 8, 12, 16, 20, 24, 28, 32, 36, 40, 44, 48, etc. mm being formed on the second surface 130B. Since each surface 130A, 130B only includes every other marking, the markings can be made twice as large and still fit without overlapping adjacent markings.

The guide can include markings having a text height that is greater than, e.g., at least twice, the adjustment increment of the guide. The guide can include markings having a text width that is at least twice the adjustment increment of the guide. The guide can have text markings having a height of at least 3.5 mm. The guide can have text markings having a height of at least 4 mm. The guide can have text markings having a height in the range of about 3.5 mm to about 3.9 mm. The guide can have text markings having a width of at least 3.5 mm. The guide can have text markings having a width of at least 4 mm. The guide can have text markings having a width in the range of about 3.5 mm to about 3.9 mm. The guide can be configured such that all of the markings on a given surface are aligned or centered along a common axis. The guide can be configured such that all of the markings on a given surface are arranged in a single line. The guide can be configured such that the markings on a given surface are not laterally staggered. The guide can be configured such that the lateral dimension of the scale is equal or substantially equal to the height of a single marking or to the width of a single marking.

The adjustment mechanism 108 can include an adjustment knob 110. The knob 110 can be rotatably coupled to the body 104, e.g., such that the knob is rotatable relative to the body about the axis A1. The knob 110 can be non-rotatably coupled to the stem 106, e.g., such that the stem is prevented from rotating relative to the knob about the axis A1. The knob 110 can include an inner groove or recess 136 for retaining the knob to the body 104 and for movably coupling the knob to the body, as described further below. The adjustment mechanism 108 can include a bias element 138 configured to urge the knob 110 longitudinally relative to the body 104. The bias element 138 can be configured to urge the knob 110 proximally relative to the body 104 along the axis A1 as shown, or alternatively can be configured to urge the knob distally relative to the body along the axis A1. The bias element 138 can include a coil spring disposed within the knob 110 and coaxially disposed over the stem 106. A proximal end of the spring can bear against a distal-facing inner surface of the knob 110. A distal end of the spring can bear against a proximal-facing surface of the body 104, directly or via an intermediate thrust washer 140 as shown. While a coil spring 138 is shown, it will be appreciated that various other bias elements can be used instead or in addition, such as a leaf spring, wave spring, resilient compressible member, and the like.

An outer surface of the knob 110 can be knurled, ribbed, or can include other features to facilitate gripping of the knob by a user. The outer surface of the knob 110 can be asymmetric about the axis A1. For example, the outer surface of the knob 110 can include diametrically-opposed flat portions 142 and diametrically-opposed lateral wings or extensions 144. The asymmetric shape of the knob 110 can add to the intuitiveness of the depth adjustment for the user. For example, movement of the lateral extensions 144 can be readily observed by the user to quantify or determine the degree of rotation of the knob 110 as the knob is rotated. Similarly, the user can readily determine from looking at the knob 110 whether the adjustment mechanism is in a locked or neutral position or in an adjustment position. Further, the distal end of the knob 110 can include cut-outs or reliefs 146 aligned with the flat sides 142 of the knob. The reliefs 146 can allow the viewing window 134 of the body 104 to be visible to the user when the device 100 is not being actively-adjusted. During an adjustment cycle, the wings 144 of the knob 110 can be rotated into alignment with the viewing window 134 to occlude or block the window, making clear to the user that the device is between depth increments.

The knob 110 can define a central lumen therethrough. At least a portion of the central lumen can include one or more flats that engage with the flats of the stem 106 to block relative axial rotation between the knob and the stem. As shown in FIG. 1A, a proximal opening 110p of the knob 110 can include diametrically-opposed first and second flat portions that contact and bear against the opposed flat surfaces of the stem 106 when the device is assembled.

The adjustment mechanism 108 can include one or more guide pins or protrusions 112 configured to interact with a corresponding guide slot or groove 114 of the body 104. For example, one or more pins 112 can be disposed in the knob 110 such that they project radially-inward into an interior cavity of the knob. The knob 110 can include first and second diametrically-opposed pins 112A, 112B as shown. The pins 112 can be welded, press-fit, or otherwise assembled to the knob 110. The pins 112 can be formed integrally with the knob 110, e.g., by directly molding or machining protrusions into the interior of the knob.

The body 104 can include a retention feature for securing the knob 110 to the body. For example, the body 104 can include one or more tabs 148 having protrusions 150 thereon for engaging with a corresponding recess 136 of the knob 110. Each tab 148 can be defined by longitudinal cuts formed in the body 104 to define a flexible cantilevered portion. The protrusion 150 of the tab 148 can be formed at the free end of the cantilevered portion. During assembly, the tabs 148 can be deflected radially-inward as the knob 110 is advanced over the body 104. Once the protrusions 150 of the tabs 148 are longitudinally-aligned with the recess 136 of the knob 110, the tabs can spring radially-outward to position the protrusions within the recess. It will be appreciated that the illustrated coupling is exemplary, and that various other features or techniques can be used to couple the knob 110 to the body 104. The recess 136 of the knob 110 can extend about the entire inner circumference or perimeter of the knob, such that the knob is capable of 360 degree rotation relative to the body 104 when assembled thereto. The recess 136 of the knob 110 can have a longitudinal height that is greater than a corresponding dimension of the tab protrusions 150, such that the knob can translate axially relative to the body 104 when assembled thereto. The height of the recess 136 relative to the height of the protrusions 150 can define the throw or range of longitudinal movement of the knob 110 relative to the body 104.

As described further below, the guide 100 can be positioned in a state of assembly in which the tabs 148 are prevented from disengaging from the knob 110. For example, once the stem 106 is threaded into the body 104 to a certain depth, the thread 124 of the stem can interfere with radially-inward movement of the tabs 148, thereby maintaining the tabs in engagement with the knob 110 and preventing inadvertent disassembly or slipping of the device during use. The stem 106 can include an unthreaded portion 128, e.g., at a distal-most end thereof, that can be longitudinally aligned with the tabs 148 to allow disassembly. In particular, the lack of thread on the unthreaded portion 128 can provide sufficient clearance for the tabs 148 to deflect radially-inward, moving the protrusions 150 out of engagement with the recess 136 of the knob 110 such that the knob can be removed from the body 104. The longitudinal length of the unthreaded portion 128 can be calibrated with the length of the stem 106 and the placement of the depth scale markings such that, once a zero or positive depth setting is reached, it is ensured that the thread 124 of the stem is longitudinally-aligned with the tabs 148 to block disassembly.

Figure 1E:
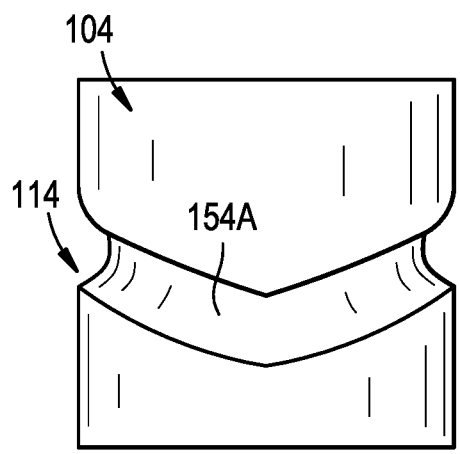
FIG. 1E is a detail right side view of a guide groove of the drill guide of FIG. 1A.
Figure 1F:
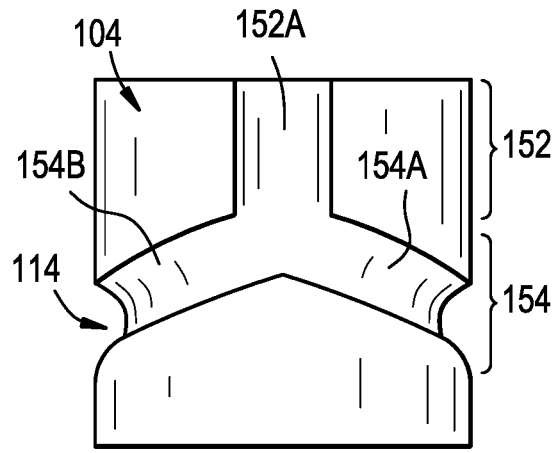
FIG. 1F is a detail top view of the guide groove of FIG. 1E.
Figure 1G:
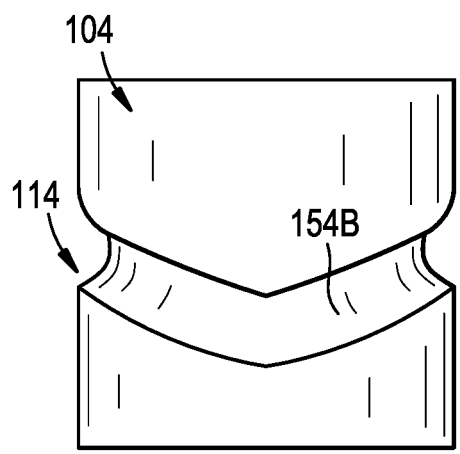
FIG. 1G is a detail left side view of the guide groove of FIG. 1E.
Figure 1H:
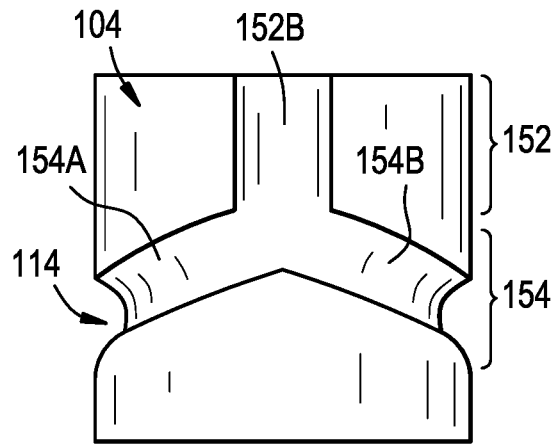
FIG. 1H is a detail bottom view of the guide groove of FIG. 1E.

The body 104 can include a groove 114 that interacts with the adjustment mechanism 108 to provide controlled depth adjustment. FIGS. 1E-1H illustrate an exemplary geometry of the groove 114. FIG. 1E is a right side view of the groove 114, FIG. 1F is a top view of the groove, FIG. 1G is a left side view of the groove, and FIG. 1H is a bottom view of the groove. Thus, FIGS. 1E-1H show the groove 114 as seen from four vantage points spaced 90 degrees apart from one another about the circumference of the body 104.

The groove 114 can be formed in an exterior surface of the body 104, e.g., adjacent a proximal end of the body as shown. The groove 114 can extend completely around the circumference or perimeter of the body 104. The groove can include a safety or locking region 152 and an adjustment region 154. The locking region 152 can be defined by opposed vertical or longitudinal portions 152A, 152B. When the guide pins 112A, 112B of the knob 110 are disposed in these vertical portions 152A, 152B of the groove 114, the knob and the stem 106 can be prevented from rotating relative to the body 104, thereby maintaining a fixed depth setting. The adjustment region 154 can be defined by opposed circumferential portions 154A, 154B of the groove 114 that connect the opposed vertical portions 152A, 152B. The circumferential portions 154A, 154B can be sloped, curved, or obliquely angled relative to a transverse plane of the body 104. For example, each circumferential portion 154A, 154B can include a quarter-turn helical down thread and a quarter-turn helical up thread. The down thread and the up thread can be opposite to one another in direction, e.g., such that the down thread is a right hand thread and the up thread is a left hand thread or vice versa. The circumferential portions 154A, 154B can be chevron-shaped and can be referred to herein as chevrons.

The sloped nature of the circumferential portions 154A, 154B, e.g., in combination with the bias element 138, can automatically return the guide pins 112 to the locking region 152 of the groove 114. For example, if user input force is released from the knob 110 while the guide pins 112 are disposed in the circumferential portions 154A, 154B of the groove 114, the bias element 138 can urge the pins to follow the groove back to the locking region 152 of the groove, rotating the stem 106 to the previous adjustment setting (if the apex of the chevron was not reached) or into the next adjustment setting (if the guide pins moved past the apex of the chevron). This can prevent the device 100 from being left in a state of partial or incomplete adjustment. While helical circumferential portions 154A, 154B are shown, in other arrangements, the circumferential portions can be defined by a straight cut that is parallel to a transverse plane of the body 104.

The geometry of the adjustment region 154 can be configured to only allow depth adjustment by one increment at a time, e.g., by automatically returning the guide pins 112 to the locking region 152 of the groove 114 between each depth increment. In the illustrated arrangement, the depth is adjusted by (1) sliding the knob 110 distally along the body 104 to move the guide pins 112 out of the locking region 152 of the groove 114, (2) rotating the knob relative to the body to cause the guide pins to traverse the adjustment region 154 of the groove and to rotate the stem 106 within the body to advance or retract the stem relative to the body, and (3) returning the knob proximally to move the pins back into the locking region of the groove.

The body 104 can include a viewing window 134 through which depth scale markings of the stem 106 can be viewed by a user. The window 134 can be defined by an opening through the sidewall of the body 104 or by a transparent or translucent portion of the body. As the stem 106 rotates and moves longitudinally relative to the body 104 during an adjustment cycle, a different one of the depth markings can be aligned with the viewing window 134. The user can thus readily observe the current depth setting by observing the marking currently aligned with the window 134. Since the stem 106 rotates relative to the window 134 during adjustment, the markings of the stem can be spread across multiple surfaces of the stem, which surfaces can be selectively aligned with the window. Accordingly, the space available for forming markings on the stem 106 can be multiplied by the number of surfaces. This is in contrast to traditional guides in which the available area is limited to a single surface and the markings must be compressed to fit on said surface. Further, the available space of the guide 100 can be increased without requiring that the user shift their eye gaze from a single point, e.g., from the window 134.

FIGS. 2A-2E schematically illustrate an exemplary adjustment sequence of the drill guide 100.

As shown in FIG. 2A, the drill guide 100 can be positioned in an initial depth setting. While a zero depth setting is shown, it will be appreciated that an adjustment cycle can be initiated from any starting setting. In the initial depth setting, the knob 110 is positioned in a relatively proximal position relative to the body 104 along the axis A1. The knob 110 is biased towards this position by the bias element 138. In the proximal position of the knob 110, the guide pins 112 are disposed in the locking region 152 of the groove 114. This positioning prevents the knob 110 from being rotated relative to the body 104, thereby preventing the stem 106 from rotating relative to the body and preventing the depth setting of the guide 100 from being adjusted. In the position shown in FIG. 2A, a first 130A of the two flat surfaces of the stem 106 is rotationally-aligned with the viewing window 134 of the body 104. The wings 144 of the knob 110 do not block the viewing window 134, such that the current depth setting of the guide 100 can be readily observed by the user.

FIG. 2B illustrates a first component of a compound user input movement required to adjust the depth setting of the guide 100. As shown, a user input force can be applied to the knob 110 to translate the knob distally relative to the body 104 along the axis A1. Distal movement of the knob 110 can compress the bias element 138 and move the guide pins 112 out of the locking region 152 of the groove 114 and into the adjustment region 154. At this point of the adjustment sequence, the knob 110 and the stem 106 have not rotated relative to the body 104, and therefore no change in the depth setting has occurred. The stem 106 (and the scale printed or formed thereon) has not moved relative to the body 104, so the initial depth marking ("0" in this example) remains visible in the viewing window 134 and is not occluded by the knob 110. In this step, the knob 110 can translate distally relative to the body 104 by a first amount, e.g., +2.5 mm.

Figure 2C:
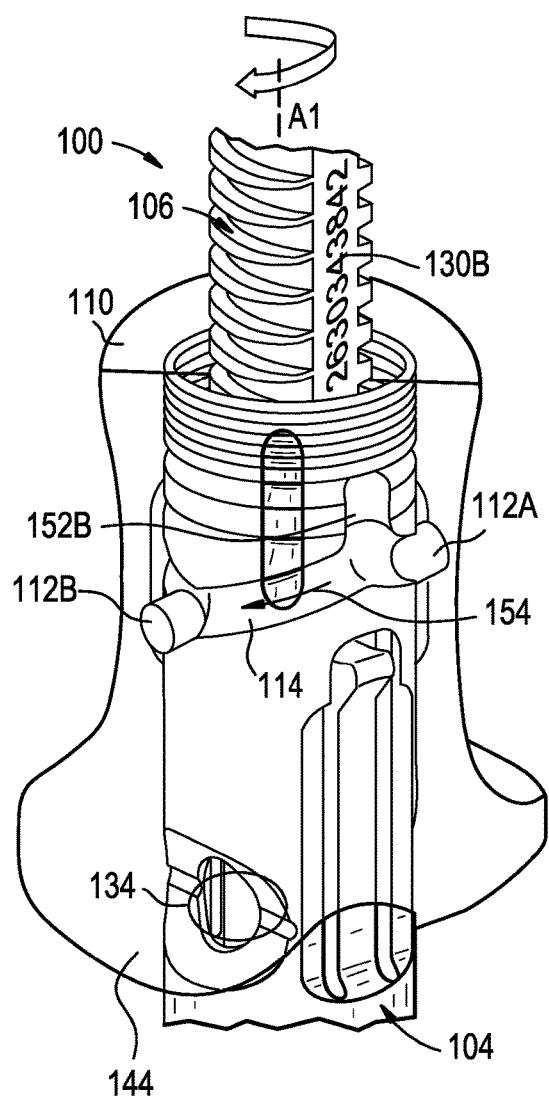

FIG. 2C illustrates a second component of the compound user input movement. As shown, a user input force can be applied to the knob 110 to rotate the knob 90 degrees relative to the body 104 about the axis A1. Rotation of the knob 110 causes the guide pins 112 to traverse the down thread portions of the chevron groove 154, causing the knob to translate distally relative to the body 104 by a second amount, e.g., +0.5 mm for a total distal translation of +3.0 mm. Rotation of the knob 110 also causes the stem 106 to rotate relative to the body 104 and thereby to be threaded into the body, advancing the stem distally by a first amount, e.g., +1.0 mm, to provide a corresponding adjustment in the depth setting of the guide 100. Rotation of the stem 106 moves the initial depth marking out of alignment with the viewing window 134. Rotation of the knob 110 moves a wing portion 144 of the knob over the viewing window 134, to temporarily occlude the viewing window and prevent any possible user confusion as the displayed marking is changing.

Figure 2D:
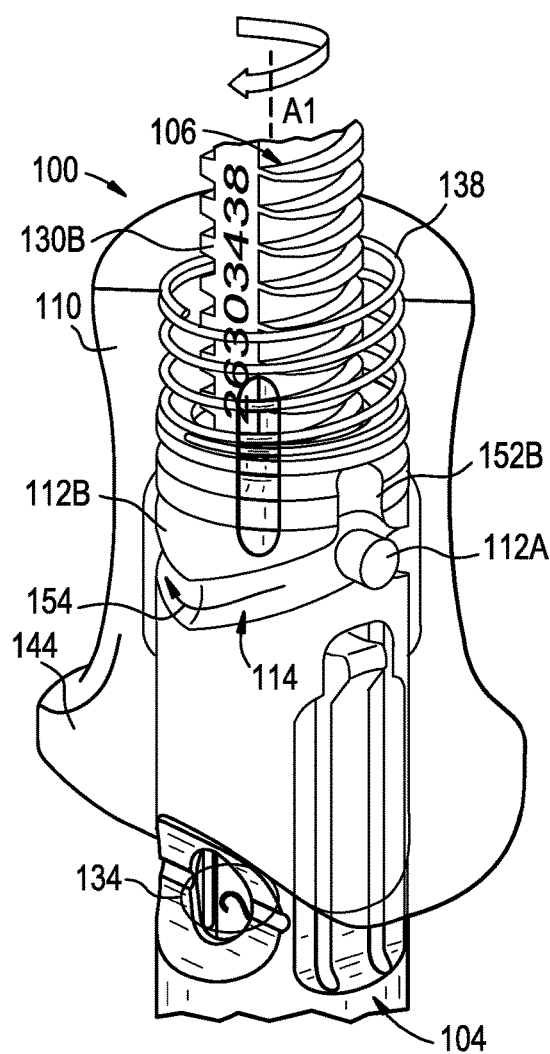

FIG. 2D illustrates a third component of the compound user input movement. As shown, a user input force can be applied to the knob 110 to rotate the knob an additional 90 degrees relative to the body 104 about the axis A1. Alternatively, or in addition, the user can simply release the knob 110 once it is rotated past the apex of the chevron 154, allowing the bias element 138 and the up-slope of the chevron to complete the 90 degree rotation. Rotation of the knob 110 causes the guide pins 112 to traverse the up thread portions of the chevron groove 154, causing the knob to translate proximally relative to the body 104 by the second amount, e.g., −0.5 mm. Rotation of the knob 110 also causes the stem 106 to rotate relative to the body 104 and thereby to be threaded into the body, advancing the stem distally by a second amount, e.g., +1.0 mm for a total distal translation of +2.0 mm, to provide a corresponding adjustment in the depth setting of the guide 100. Rotation of the stem 106 moves the next incremental depth marking into alignment with the viewing window 134 ("2" in this example). Rotation of the knob 110 moves the wing portion 144 of the knob away from the viewing window 134, once again exposing the window to allow the depth setting to be readily observed. In the position shown in FIG. 2D, a second 130B of the two flat surfaces of the stem 106 is rotationally-aligned with the viewing window 134 of the body 104.

Figure 2E:
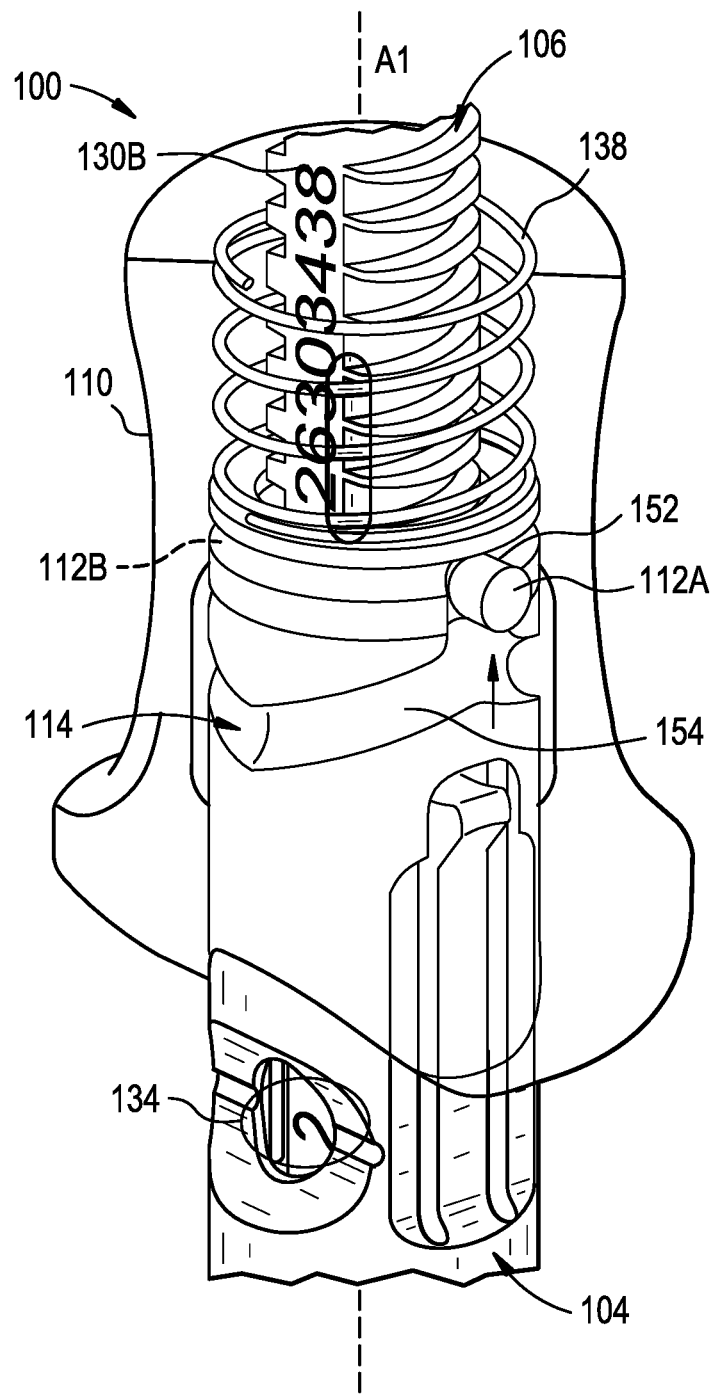

FIG. 2E illustrates a fourth component of the compound user input movement. As shown, a user input force can be applied to the knob 110 to translate the knob proximally relative to the body 104 along the axis A1. Alternatively, or in addition, the user can simply release the knob 110, allowing the bias element 138 to move the knob proximally along the body 104. Proximal movement of the knob 110 can decompress the bias element 138 and move the guide pins 112 out of the adjustment region 154 of the groove 114 and into the locking region 152. The knob 110 and the stem 106 do not rotate relative to the body 104 during this step, such that the depth setting of the guide 100 does not change and the current depth setting ("2" in this example) remains visible in the window 134. The knob 110 can translate proximally relative to the body 104 by the first amount, e.g., −2.5 mm. In the position shown in FIG. 2E, the knob 110 is returned to the relatively proximal position shown in FIG. 2A. In the proximal position of the knob 110, the guide pins 112 are disposed in the locking region 152 of the guide groove 114. This positioning prevents the knob 110 from being rotated relative to the body 104, thereby preventing the stem 106 from rotating relative to the body and preventing the depth setting of the guide 100 from being adjusted. In the position shown in FIG. 2E, the second 130B of the two flat surfaces of the stem 106 is rotationally-aligned with the viewing window 134 of the body 104.

In the adjustment cycle shown in FIGS. 2A-2E, the knob 110 translates distally relative to the body 104 by a certain amount (+3.0 mm in this example) and then returns proximally by the same amount (−3.0 mm in this example). Accordingly, there is no net change in the longitudinal position of the knob 110 relative to the body 104 before and after the adjustment cycle. The knob 110 rotates 180 degrees relative to the body 104 over the course of the adjustment cycle. In this example, distal axial translation of the knob corresponds to a user pushing forward on the knob during use. In other arrangements, the guide 100 can be configured to require pulling back on the knob, creating a proximal axial translation that then is biased to return distally.

In the adjustment cycle shown in FIGS. 2A-2E, the stem 106 translates distally relative to the body 104 by a certain amount (+2.0 mm in this example) and remains in that position when the cycle is complete. Accordingly, there is a net change in the longitudinal position of the stem 106 relative to the body 104 before and after the adjustment cycle, representing the net change in the depth setting of the guide 100. The stem 106 rotates 180 degrees relative to the body 104 over the course of the adjustment cycle. Accordingly, where a first surface 130A of a multi-surface depth scale is aligned with the viewing window 134 prior to the cycle, a different, second surface 130B of the multi-surface depth scale is aligned with the viewing window after the cycle.

FIGS. 3A-3J schematically illustrate an exemplary method of assembling the drill guide 100.

Figure 3A:
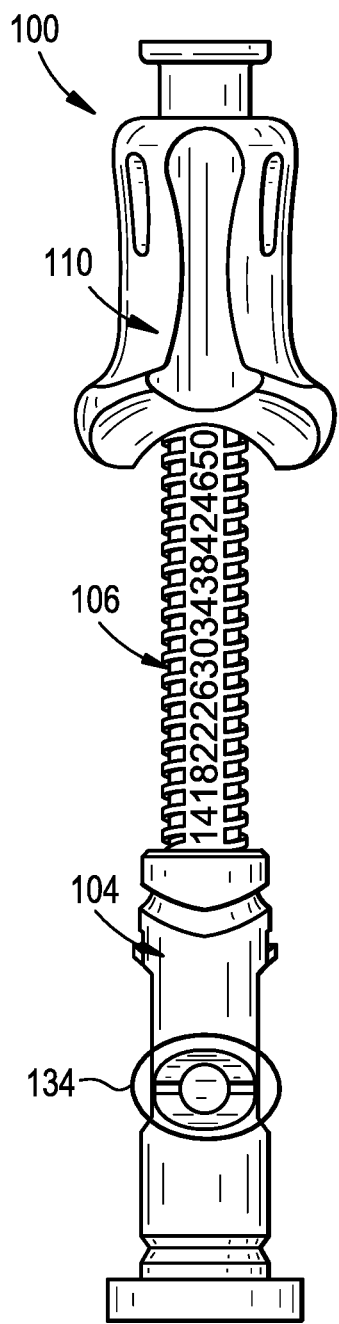
Figure 3B:
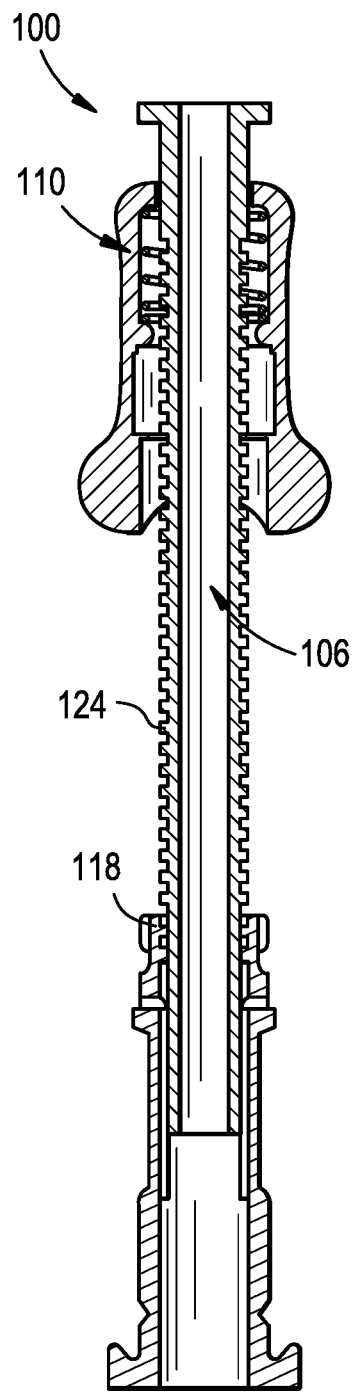

As shown in FIGS. 3A-3B, the distal end of the stem 106 can be inserted into a proximal opening of the knob 110 and the knob can be slid proximally along the stem. The distal end of the stem 106 can then be inserted into the proximal end of the body 104 until the thread 124 of the stem begins to engage the thread 118 of the body. At this stage of assembly, the depth markings of the stem 106 are not yet visible in the window 134 of the body 104.

As shown in FIGS. 3C-3D, the stem 106 can be rotated to thread the stem into the body 104 until a first assembly marking ("A" in this example) is visible in the window 134. The first assembly marking can indicate to the user that the stem 106 and the body 104 are in an appropriate relative longitudinal position for assembly of the knob 110 to the body. The first assembly marking can also indicate to the user that the knob 110 and the body 104 are in an appropriate relative rotational position for assembly of the knob to the body, e.g., to indicate that the pins 112 are aligned with the vertical locking portions 152 of the groove 114.

As shown in FIGS. 3E-3F, the knob 110 can then be slid distally along the stem 106 and down onto the body 104. As the knob 110 slides onto the body 104, the tabs 148 of the body can deflect radially inward until they are aligned with the recess 136 of the knob, at which point the tabs can spring outward into engagement with the recess, thereby retaining the knob to the body. As shown in FIG. 3F, the unthreaded portion 128 of the stem 106 can be aligned with the tabs 148 at this stage of assembly, such that the stem does not interfere with or block radially-inward movement of the tabs. At this stage of assembly, the guide pins 112 of the knob 110 are inserted into the locking region 152 of the guide groove 114 of the body 104. The bias element 136 or washer 140 is seated against the proximal shoulder of the body 104, with little if any compression of the spring. The first assembly marking remains visible in the window 134. The body 104 and the knob 110 can include keying features to ensure that the knob is only attachable to the body in one orientation during initial assembly. For example, the body 104 can include a protrusion that is received in a groove formed in the knob 110. This can ensure that the stem 106 starts in the correct orientation and prevents the stem from threading into the body 104 with the wrong side of the stem facing the viewing window 134.

As shown in FIGS. 3G-3H, a depth adjustment maneuver can be performed as described above with respect to FIGS. 2A-2E to advance the stem 106 by one increment into the body 104. Once the stem 106 is advanced, a second assembly marking ("B" in this example) is visible in the window 134. The depth adjustment maneuver can be repeated as many times as needed until the thread 124 of the stem 106 begins to interfere with radially-inward movement of the tabs 148.

As shown in FIGS. 3I-3J, the stem 106 can be advanced until the thread 124 of the stem blocks radially-inward movement of the tabs 148. In some embodiments, this can require three 180 degree rotations of the knob 110 after the knob is initially assembled to the body 104. With this relative positioning of the stem 106 and the body 104, the "0" marking of the stem can be visible in the window 134. This can indicate to a user that assembly is complete and that the drill guide 100 is in the zero position and ready for use. The zero position can be one in which a drill designed to be used with the drill guide 100 would be flush with the distal end of the body 104 when the drill is inserted all the way to the proximal stop of the drill guide. In other words, in the zero position, the maximum insertion depth of the drill can be aligned with the distal end of the body 104, such that the drill does not protrude distally beyond the distal end of the body and is not recessed proximally relative to the distal end of the body. With the thread 124 of the stem 106 blocking radially-inward movement of the tabs 148, the tabs cannot disengage from the knob 110 and therefore disassembly of the guide 100 is prevented by secure attachment of the knob to the body 104. In the illustrated arrangement, the guide 100 can only be disassembled by lengthening the sleeve 102 to a depth setting that is less than zero.

With the drill guide 100 assembled and ready for use, the user can perform the adjustment maneuver described above with respect to FIGS. 2A-2E to advance or retract the stem 106 from the body 104 and thereby adjust the depth setting of the drill guide. The adjustment maneuver can be performed as many times as needed to reach the desired setting. For example, to increase the depth setting by five increments, the adjustment maneuver can be performed five times, rotating the knob 110 the same direction each time (e.g., in a clockwise direction from the user's perspective). As another example, to decrease the depth setting by three increments, the adjustment maneuver can be performed three times, rotating the knob 110 the same direction each time (e.g., in a counterclockwise direction from the user's perspective).

The above steps can be performed in reverse order to disassemble the drill guide 100. For example, the adjustment maneuver can be performed to return the drill guide 100 to the zero setting, at which point subsequent maneuvers can be effective to unthread the stem 106 from the body 104 and align the unthreaded portion 128 of the stem with the tabs 148. With the tabs 148 now free to deflect radially-inward, a proximally-directed force can be applied to the knob 110 to remove it from the body 104. The stem 106 can then be unthreaded completely from the body 104 to complete the disassembly.

The drill guides described herein can be used without a handle, e.g., as shown in FIG. 1A. In some embodiments, the drill guide can include or can be used with a handle. The handle can extend in a generally lateral direction from the drill guide, such that the handle is perpendicular or obliquely angled relative to the axis A1. The handle can be grasped by a user to stabilize or manipulate the drill guide. The handle can be configured for attachment with a surgical robot, e.g., with an arm of the robot programmed to position the drill guide for use in a surgery. The handle can be configured for attachment to a stationary support, such as an articulating support arm coupled to the operating table or to a floor, ceiling, or wall of the operating room. The handle can be configured for selective attachment and detachment from the drill guide as needed or desired during the course of a procedure. The handle can be adjustable, e.g., such that the handle can be moved between any of a plurality of rotational positions about the axis A1, and/or between any of a plurality of positions along the length of the drill guide. In the case of the drill guide 100, the handle can be coupled to the body 104, to the stem 106, to the knob 110, or to multiple of said components. The handle can be interchangeably couple-able to any of the body 104, the stem 106, and the knob 110.

Figure 4A:
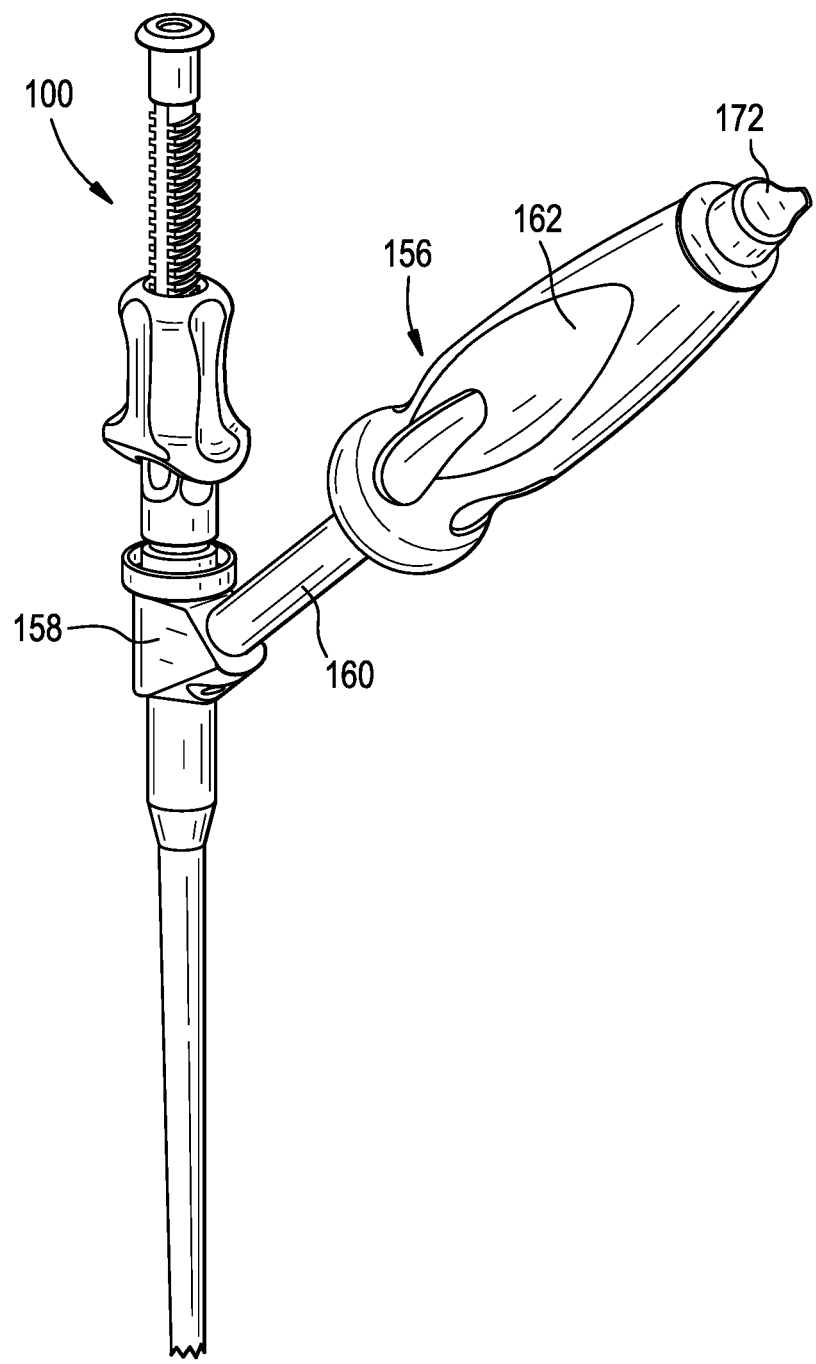
FIG. 4A is a perspective view of the drill guide of FIG. 1A with an attached handle.

FIG. 4A illustrates an exemplary handle 156 that can be used with the drill guide 100. The handle 156 can include a distal housing 158 that defines a longitudinal opening through which the drill guide 100 can be inserted. The distal housing 158 can be ring-shaped. The handle 156 can include a main shaft or body 160 extending proximally from the distal housing 158. The handle 156 can include a proximal grasping portion or grip 162 configured to be held by a user.

The handle 156 can include a mating feature that interacts with a counterpart mating feature of the drill guide 100 to secure the handle thereto.

Figure 4B:
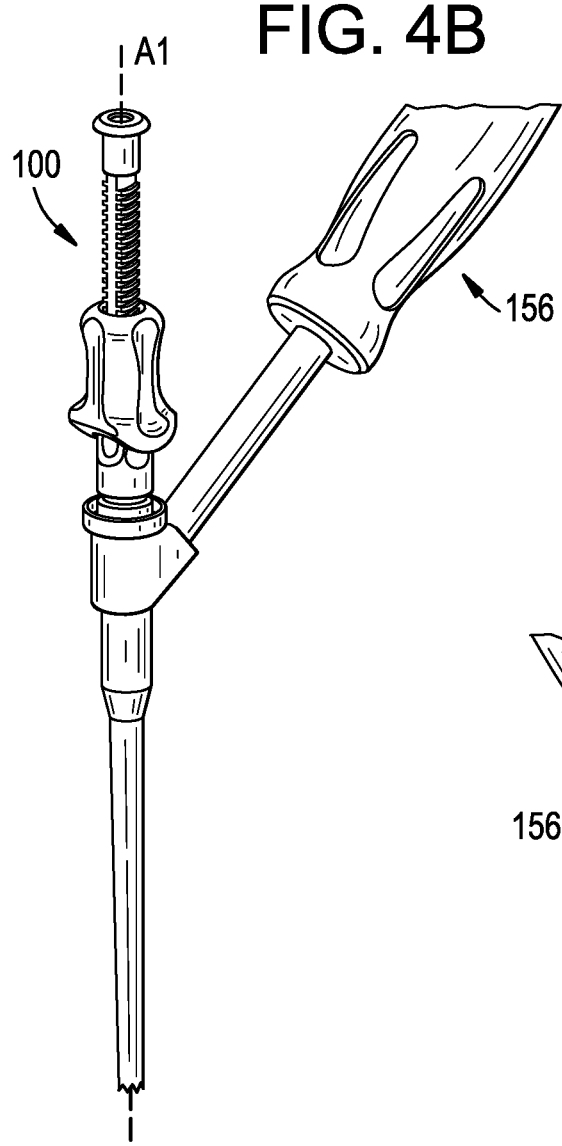
FIG. 4B is a perspective view of the handle and drill guide of FIG. 4A in another position.
Figure 4C:
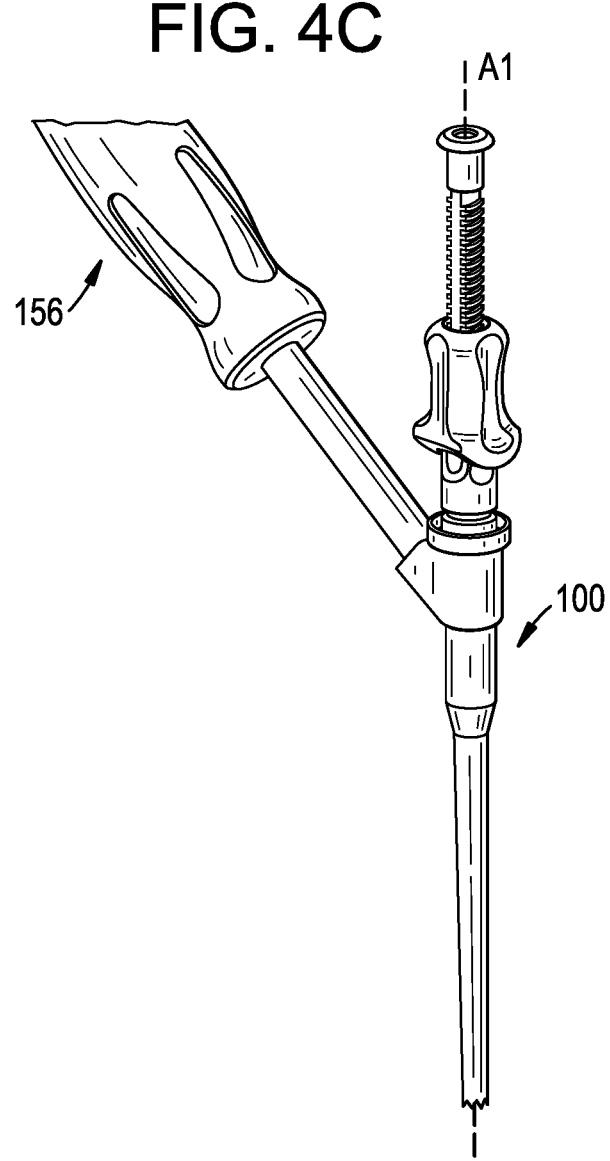
FIG. 4C is a perspective view of the handle and drill guide of FIG. 4A in yet another position.

As shown in FIGS. 4B and 4C, the handle 156 can be selectively positioned relative to the drill guide 100 in any of a variety of rotational positions about the axis A1. The mating features of the handle 156 and the drill guide 100 can be configured such that the handle can be positioned in any of a number of discrete positions relative to the drill guide, e.g., at 90 degree intervals about the circumference of the drill guide. In other arrangements, the mating features of the handle 156 and the drill guide 100 can be configured such that the handle can be positioned in any of an infinite number of positions relative to the drill guide.

Figure 4D:
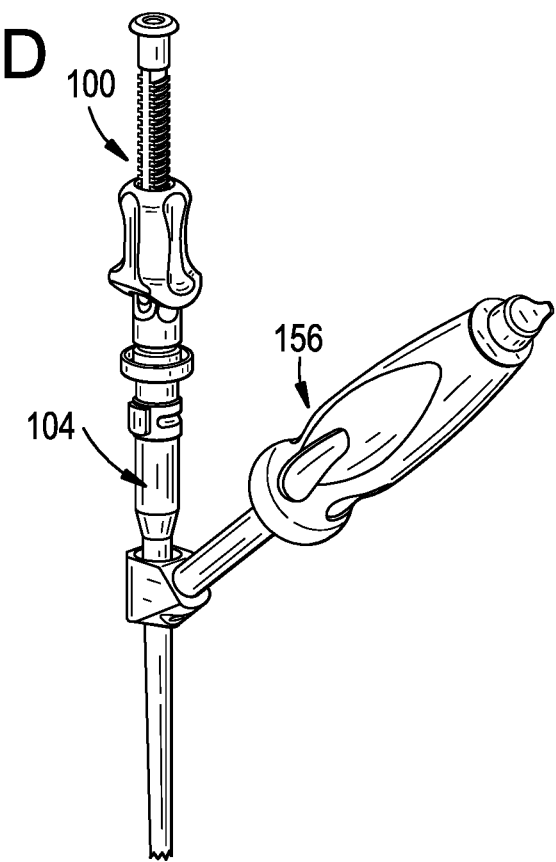
FIG. 4D is a perspective view of the handle and drill guide of FIG. 4A schematically illustrating assembly of the handle to the drill guide.

As shown in FIG. 4D, the handle 156 can be loaded distally onto the drill guide 100, e.g., by loading a distal end of the drill guide into a proximal end of the handle and sliding the handle proximally along the drill guide. In other arrangements, the handle 156 can be loaded proximally onto the drill guide 100.

FIGS. 4E-4I illustrate an exemplary mechanism for selectively attaching a handle to a drill guide. It will be appreciated that various other attachment mechanisms can be used instead or in addition.

Figure 4E:
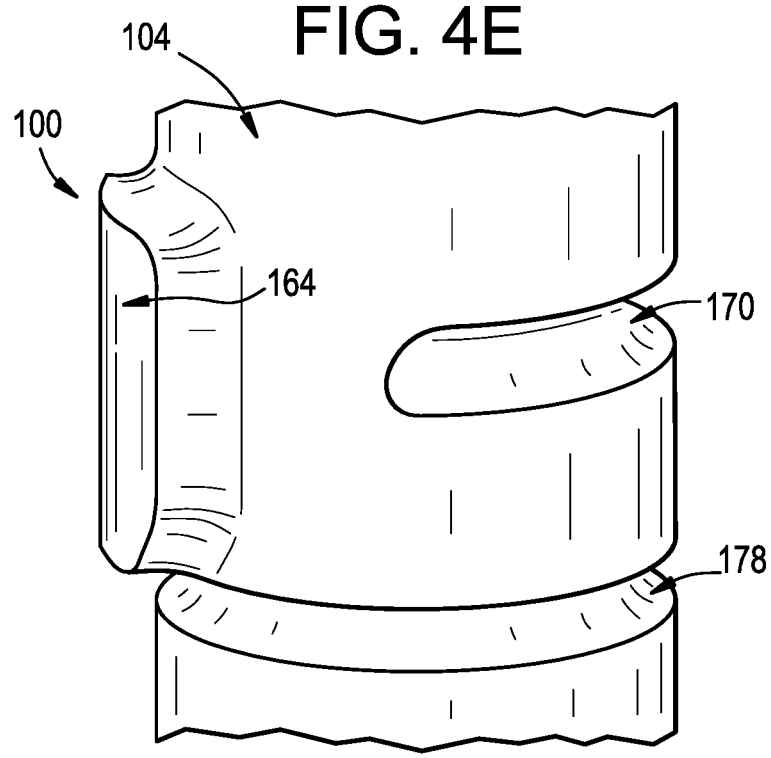
FIG. 4E is a detail perspective view of a handle mating feature of the drill guide of FIG. 4A.

As shown in FIG. 4E, the body 104 of the drill guide 100 can include mating features for interacting with mating features of the handle 156. For example, the body 104 can include a protrusion or lug 164 configured to be received within a counterpart groove or recess of the handle 156. The handle 156 can include a plurality of counterpart recesses, each associated with a respective discrete rotational portion of the handle relative to the drill guide 100. Thus, the lug 164 can be inserted into a first groove of the handle housing 158 to position the handle at a 0 degree position about the axis A1, into a second groove of the handle housing to position the handle at a 90 degree position about the axis A1, into a third groove of the handle housing to position the handle at a 180 degree position about the axis A1, and so forth. To switch handle positions, the handle housing 158 can be slid distally along the axis A1 to move the lug 164 out of the handle recess. The handle 156 can then be freely rotated about the axis A1 to align another of the handle recesses with the lug 164. The handle housing 158 can then be returned proximally along the axis A1 to move the lug 164 into the newly-selected recess.

As shown in FIGS. 4F-4I, the handle 156 and/or the drill guide 100 can include features to selectively lock axial translation between the handle and the drill guide, and thus selectively lock the above-described handle repositioning. For example, the handle 156 can include a central locking shaft 166 disposed within a lumen of the main handle shaft 160. The locking shaft 166 can be rotatable relative to the distal housing 158 of the handle 156 about a central longitudinal axis A3 of the handle. The distal end of the locking shaft 166 can be asymmetric. For example, as shown, the distal end of the locking shaft 166 can be tapered, slash-cut, obliquely-cut, or can be similarly configured. The angle of the cut in the distal end of the locking shaft 166 can be commensurate with the angle of the axis A3 relative to the axis A1.

Figure 4F:
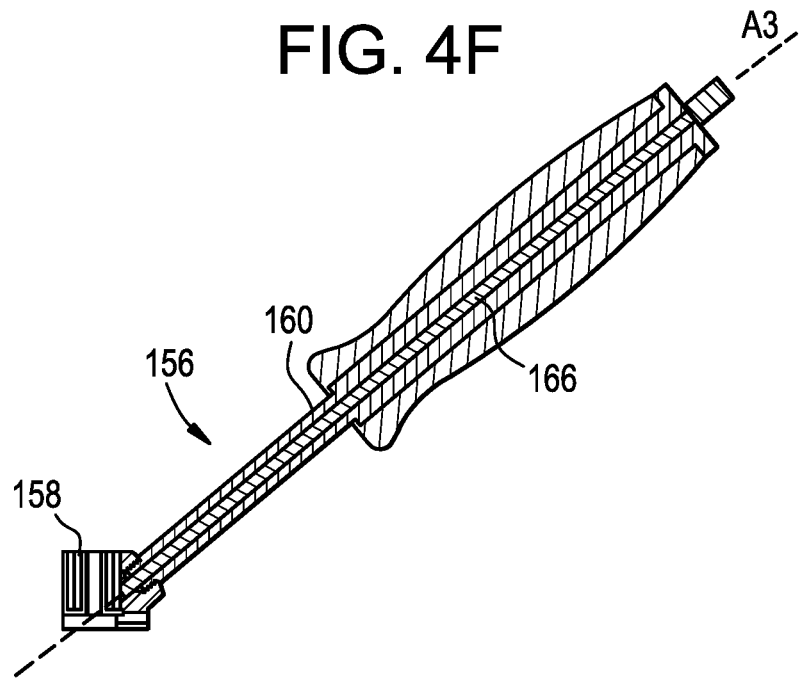
FIG. 4F is a sectional side view of the handle of FIG. 4A in an unlocked position.
Figure 4G:
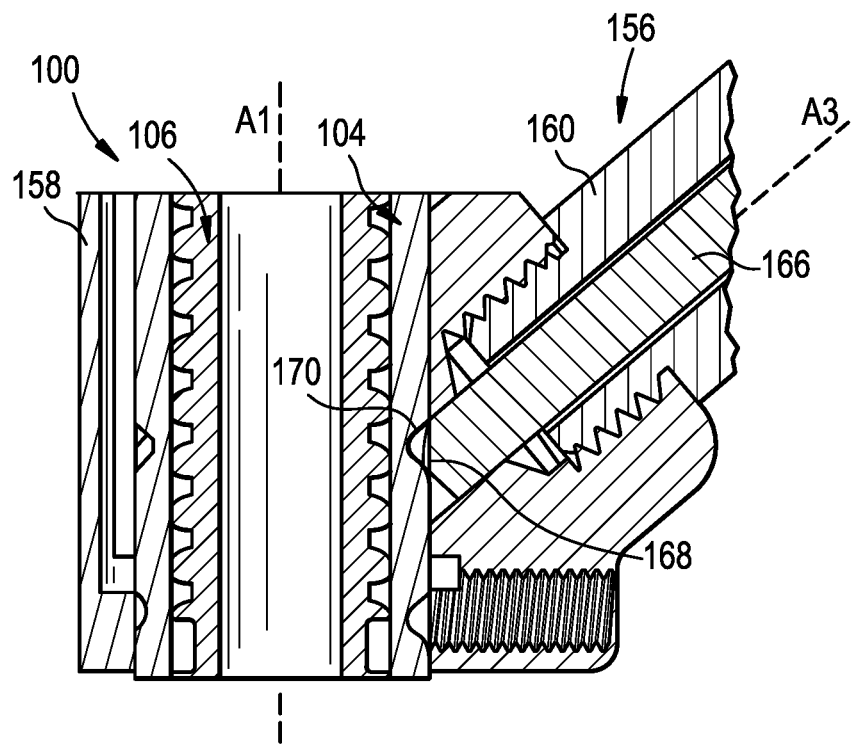
FIG. 4G is a detail sectional side view of the drill guide and handle of FIG. 4A in the unlocked position.

As shown in FIGS. 4F and 4G, the locking shaft 166 can be rotated about the axis A3 to a first, unlocked position. In the unlocked position, the cut surface 168 of the locking shaft 166 can be oriented parallel or substantially parallel to the axis A1, such that the locking shaft does not penetrate the outside diameter of the drill guide 100 and such that no portion of the locking shaft is received within a circumferential locking groove 170 formed in the outer surface of the body 104. In this position, the housing 158 of the handle 156 can be free to slide longitudinally along the outer surface of the body 104, e.g., to remove or insert the lug 164 from one of the handle recesses or to remove the handle from the drill guide 100 altogether.

Figure 4H:
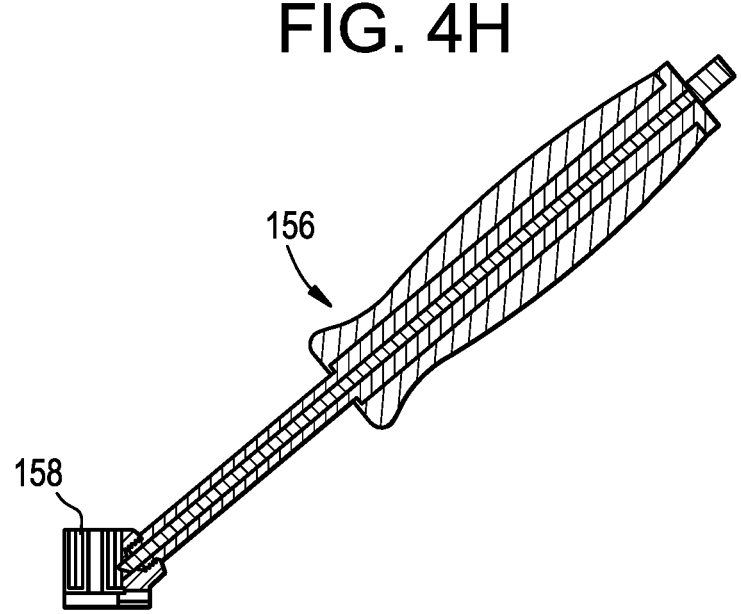
FIG. 4H is a sectional side view of the handle of FIG. 4A in a locked position.
Figure 4I:
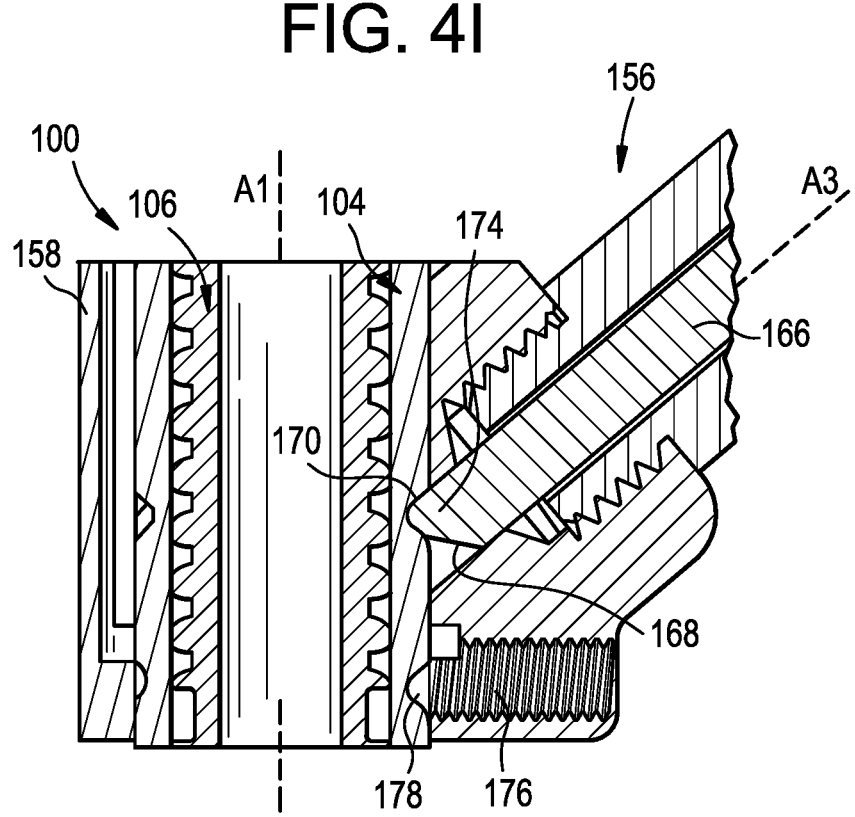
FIG. 4I is a detail sectional side view of the drill guide and handle of FIG. 4A in the locked position.

As shown in FIGS. 4H-4I, the locking shaft 166 can be rotated about the axis A3 to a second, locked position. The locked and unlocked positions of the shaft 166 can be 180 degrees apart from one another. The handle 156 can include an arrow indicator 172 (shown in FIG. 4A) or other visual, audible, or tactile feedback features for indicating the current position of the locking shaft. In the locked position, the cut surface 168 of the locking shaft 166 can be non-parallel with the axis A1 and/or oriented away from the axis A1. Accordingly, the non-cut portion 174 of the locking shaft 166 can be rotated to penetrate the outside diameter of the drill guide 100, positioning the distal non-cut portion of the locking shaft within the locking groove 170 of the body 104. In this position, interference between the locking shaft 166 and the groove 170 can prevent the housing 158 of the handle 156 from sliding longitudinally along the outer surface of the body 104, thereby maintaining the handle in a fixed position relative to the drill guide 100. Rotation of the locking shaft 166 can be controlled by a knob or other actuator. The actuator can be disposed at a proximal end of the handle 156.

As another example of a locking mechanism, the handle 156 can include a central shaft that is threaded into the outer body 160 of the handle. Relative rotation between the central shaft and the outer body 160 can advance the central shaft axially into engagement with the groove 170 of the drill guide 100 to lock the handle 156, or to withdraw the central shaft axially out of engagement with the groove to unlock the handle.

As another example of a locking mechanism, the distal handle housing 158 can include a threaded hole 176 through which a threaded locking screw can be inserted. When the handle housing 158 is disposed over the body 104 of the drill guide 100, the threaded hole 176 can be aligned with a circumferential locking groove 178 formed in the outer surface of the body. The locking screw can be advanced within the opening 176 to position a distal tip of the locking screw within the groove 178, thereby locking the handle 156 to the body 104. The locking screw can be retracted within the opening 176 to withdraw the distal tip of the locking screw from the groove 178, thereby unlocking the handle 156 and restoring free longitudinal translation between the handle and the drill guide 100.

The handle 156 can include one or more locking mechanisms. For example, the handle 156 can include only the locking shaft arrangement described above. As another example, the handle 156 can include only the locking screw arrangement described above. As another example, and as shown in FIGS. 4E-4I, the handle 156 can include both the locking shaft arrangement and the locking screw arrangement.

The drill guides disclosed herein can be used with a surgical navigation system. A typical navigation system includes an array of markers attached to a surgical instrument, an imaging system that captures images of the surgical field, and a controller that detects the markers in the captured images and tracks movement of the markers within the surgical field. The controller associates a reference frame of the imaging system with a reference frame of the patient and, informed by a known geometry of the array and the instrument, determines how the instrument is being moved relative to the patient. Based on that determination, the controller provides navigation feedback to the surgeon.

Figure 5:
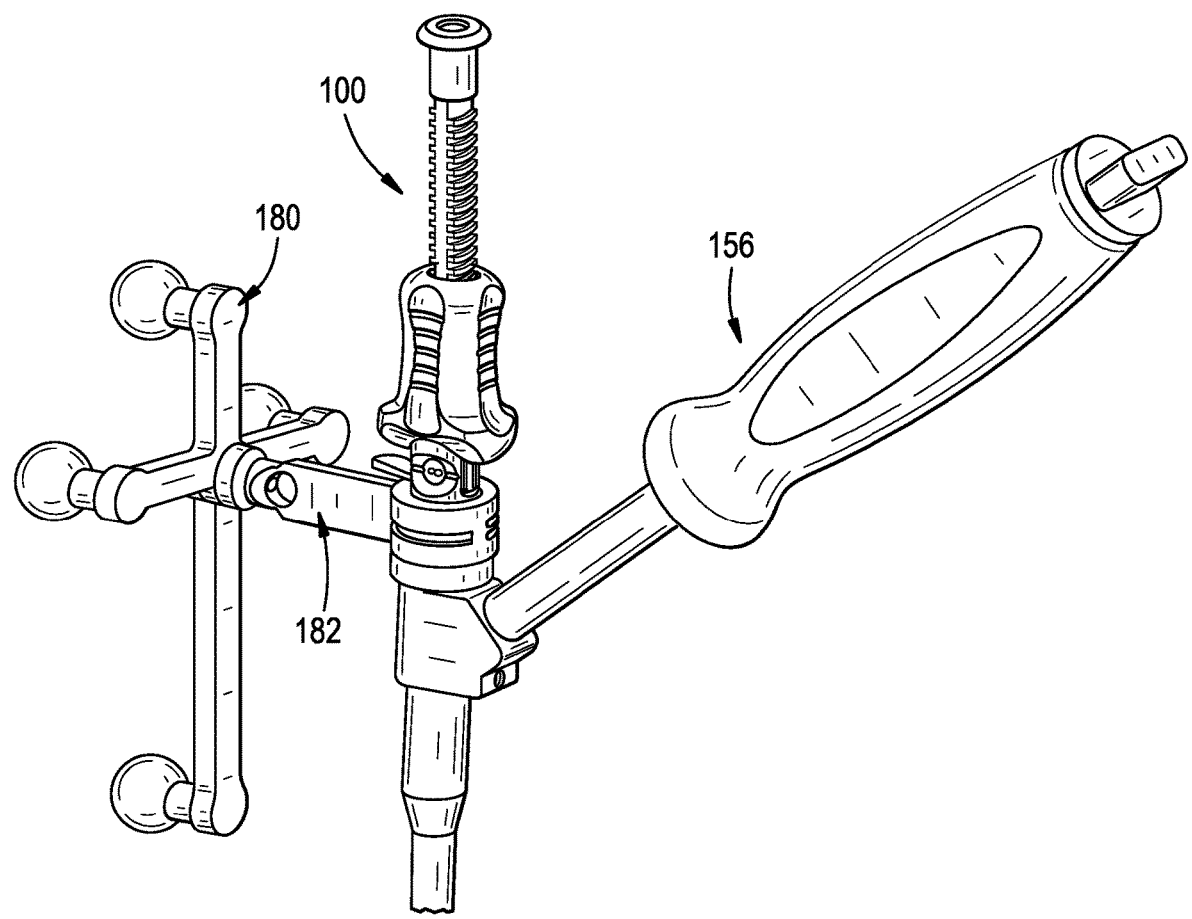
FIG. 5 is a perspective view of the drill guide of FIG. 1A with an attached coupling and navigation array.

A navigation array can be selectively attached to the drill guide, e.g., to facilitate navigated positioning of the drill guide relative to a patient. The navigation array can be formed integrally with the drill guide, can be assembled thereto, and/or can be configured for selective attachment to the drill guide. As shown in FIG. 5, the navigation array 180 can be attachable to the drill guide 100 using an instrument coupling 182. Exemplary instrument couplings are described in U.S. patent application Ser. No. 15/609,712 filed on May 31, 2017 and entitled "COUPLING DEVICES FOR SURGICAL INSTRUMENTS AND RELATED METHODS" which is hereby incorporated by reference herein. The drill guide 100 can include any of the counterpart geometries described in the above reference for attaching the instrument coupling 182 to the drill guide.

The navigation array 180 or instrument coupling 182 can be loaded proximally onto the drill guide 100. The navigation array 180 or instrument coupling 182 can be loaded distally onto the drill guide 100. The drill guide 100 can be configured to accept both proximal and distal loading of the navigation array 180 or instrument coupling 182.

Embodiments disclosed herein in which the handle 156 is adjustable relative to the drill guide 100 can advantageously allow the handle to be repositioned during use, e.g., to provide better visibility between the array 180 and the navigation system, for example when the handle 156 would otherwise occlude one or more of the array markers.

The drill guide 100 can be used with or without the navigation array 180, allowing the same drill guide to be used in navigated and non-navigated surgery. This can advantageously reduce the number of instruments that must be inventoried and prepared for a surgery, reducing costs and expenses.

FIGS. 6A-6D illustrate a protection sleeve 184 accessory that can be used with the drill guides described herein. The protection sleeve 184 can serve as a retractor or access device for accessing certain patient anatomy. For example, the protection sleeve 184 can be particularly useful when working in and around the C1 or C2 vertebrae of a patient's spine. FIG. 7 schematically illustrates an exemplary technique for applying a transarticular fixation screw 186 to the C1 vertebra via a trajectory that passes through the C2 vertebra. In this type of procedure, as well as various others, a protection sleeve 184 of the type described herein can advantageously protect delicate neural, vascular, and other anatomical structures from instruments and implants passing into and out of the surgical site. The protection sleeve 184 can be inserted along the path shown in FIG. 7, and one or more instruments can be inserted through the protection sleeve to complete the procedure. Exemplary instruments that can be inserted through the protection sleeve 184 include the drill guides described herein, e.g., the drill guide 100, screws or other implants, drills, taps, screw drivers, and so forth.

The protection sleeve 184 can be defined by generally tubular body having a proximal end 184p, a distal end 184d, and a central longitudinal axis A4 extending therebetween. The sleeve 184 can define a central lumen 186 through which implants or instruments can be inserted. The outer sidewall of the protection sleeve 184 can include a longitudinal gap or opening 188. The opening 188 can extend all the way from the proximal end 184p of the sleeve 184 to the distal end 184d of the sleeve as shown. The opening 188 can be configured such that the tubular body forms less than a complete cylinder or circumference. The outside diameter of the sleeve can be stepped or tapered at one or more locations along the length of the sleeve 184. As shown, the sleeve 184 can have a reduced diameter distal portion, an intermediate diameter central portion, and an enlarged diameter proximal portion.

The sleeve 184 can include an arm 190 that extends radially-outward from the main body of the sleeve. The arm 190 can include attachment features for attaching the sleeve 184 to a handle. For example, the arm 190 can include the attachment features of the drill guide 100 described above with respect to FIG. 4E, allowing the sleeve 184 to work with the handle 156 shown in FIGS. 4F-4I. The attachment features can be formed on a substantially cylindrical portion of the arm 190 that is offset from and parallel to the main body of the protection sleeve 184. Alternatively, or in addition, the handle attachment features can formed on the main body of the sleeve 184. The sleeve 184 can have a handle formed integrally therewith or permanently attached thereto.

The open side 188 of the protection sleeve 184 can serve as a guide track that receives a lug or protrusion of an instrument inserted through the sleeve. For example, the open track 188 can receive the lug 164 of the drill guide 100 described above when the drill guide is inserted through the protection sleeve 184. Engagement between the track 188 and the lug 164 can prevent relative rotation between the body 104 of the drill guide 100 and the protection sleeve 184.

The open side 188 of the protection sleeve 184 can allow the sleeve to be separated from an implant or instrument inserted therethrough by moving the sleeve laterally with respect thereto. In other words, certain implants or instruments inserted through the sleeve 184 can be removed therefrom by shifting the sleeve laterally relative to the implant or instrument, instead of or in addition to moving the sleeve longitudinally relative to the implant or instrument. This can advantageously allow the sleeve 184 to be released laterally from a screw or other implant having an enlarged head after the screw is driven into a bone of the patient.

Figure 6A:
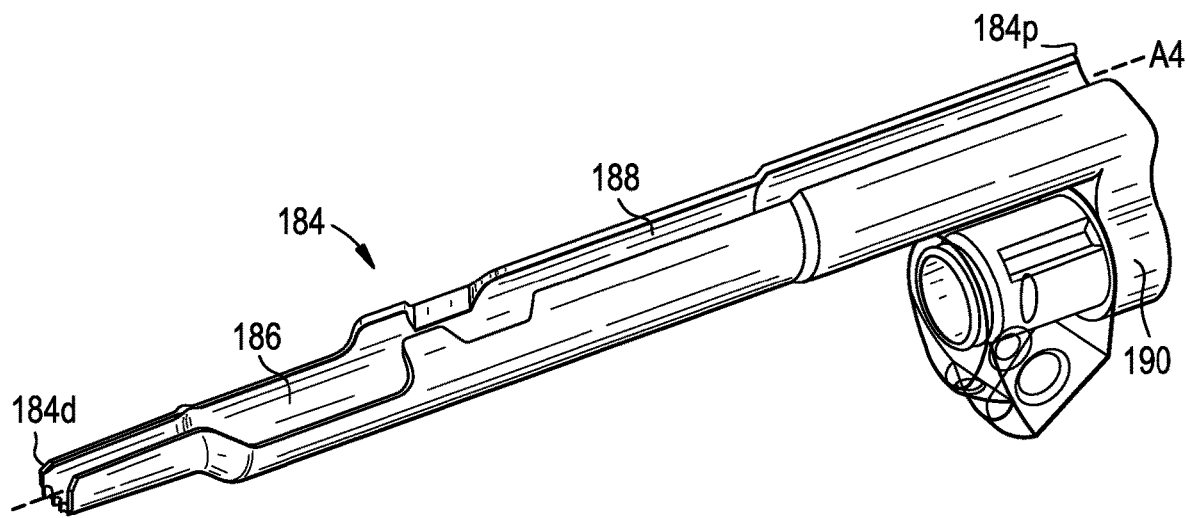
FIG. 6A is a perspective view of a protection sleeve.
Figure 6B:
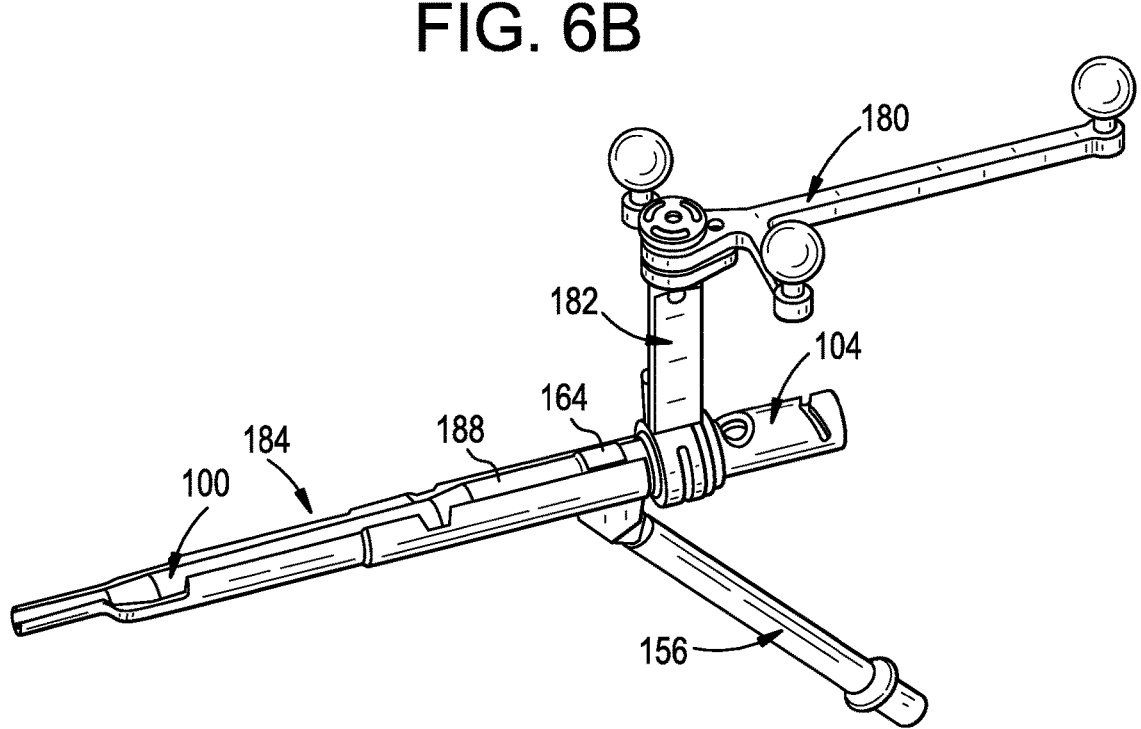
FIG. 6B is a perspective view of the protection sleeve of FIG. 6A with the drill guide of FIG. 1A inserted therethrough.
Figure 7:
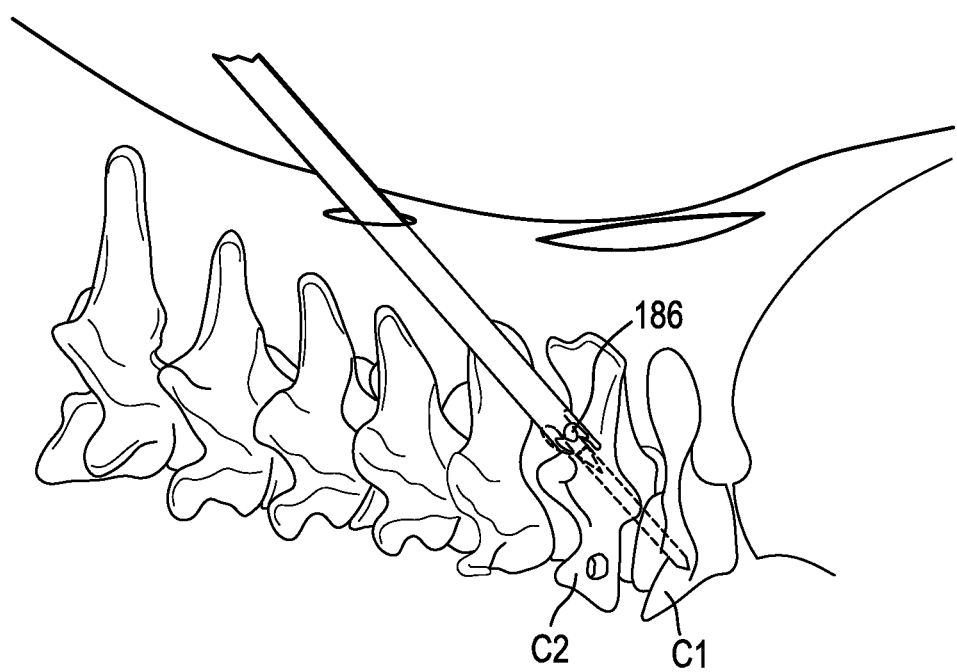
FIG. 7 schematically illustrates a protection sleeve in use to define a path for applying a screw to the C1 vertebra of a patient.

The protection sleeve 184 is shown in FIG. 6B with a drill guide 100 inserted through the sleeve. Also shown is a handle 156 of the type described in FIGS. 4F-4I attached to the arm 190 of the protection sleeve 184, as well as a navigation array 180 attached to the body 104 of the drill guide 100 via an instrument coupling 182 of the type shown in FIG. 5.

Figure 6C:
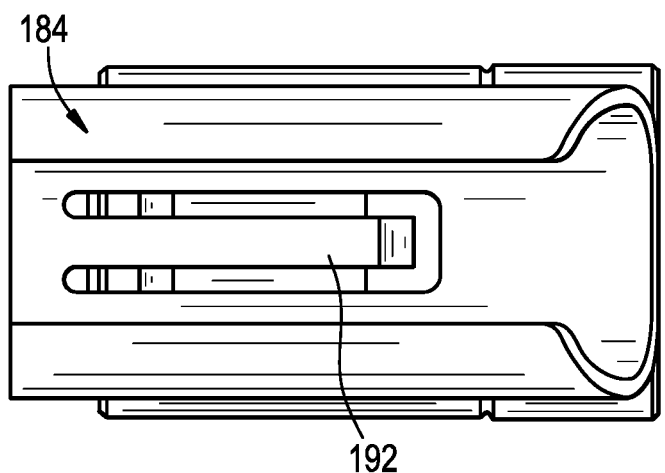
FIG. 6C is a top view of a securement feature of the protection sleeve of FIG. 6A.
Figure 6D:
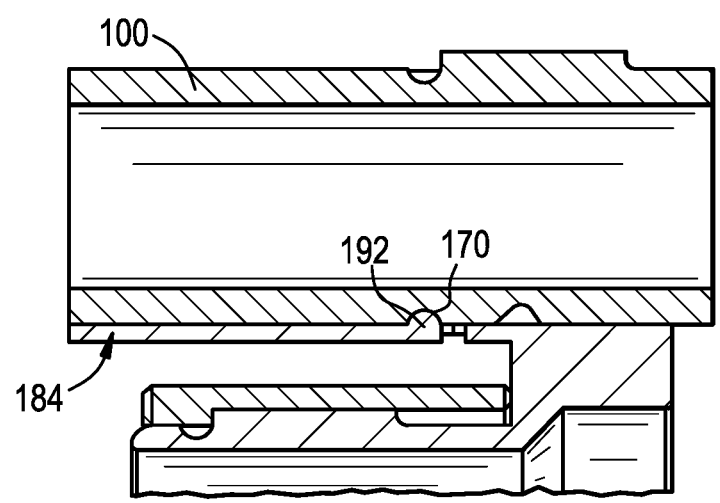
FIG. 6D is a sectional side view of the securement feature of FIG. 6C engaged with an instrument inserted through the protection sleeve.

As shown in FIGS. 6C-6D, the protection sleeve 184 can include features for securing the sleeve to an object inserted through the sleeve. For example, the protection sleeve 184 can include a wire cut through an outer sidewall thereof to define a cantilevered spring tab 192. The tab 192 can be configured to deflect radially-outward as an instrument is inserted through the protection sleeve 184, and to then snap back radially-inward into engagement with a groove or recess of the instrument. For example, as shown, the spring tab 192 can engage with one of the handle attachment grooves 170, 178 of the drill guide 100. Engagement between one or more tabs or other securement features 192 of the sleeve 184 and the instrument can prevent certain relative movement between the instrument and the sleeve, e.g., to block relative longitudinal movement and/or axial rotation.

Figure 8A:
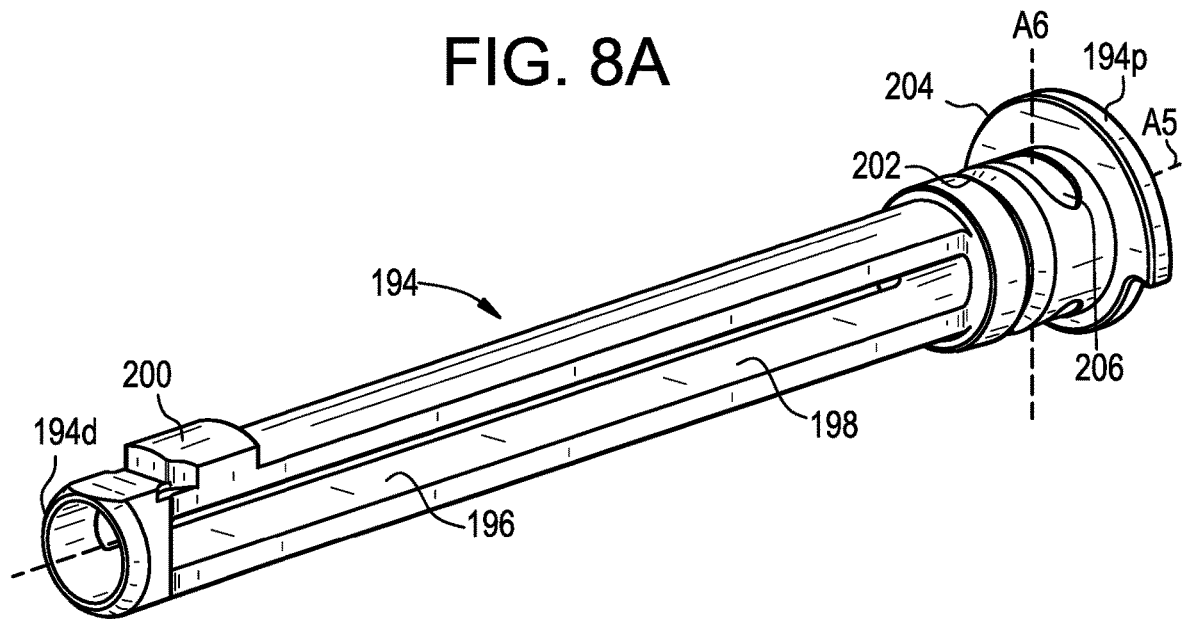
FIG. 8A is a perspective view of a navigation adapter.

FIG. 8A illustrates a navigation sleeve or adapter 194 that can be used with the drill guides and other instruments disclosed herein. The navigation adapter 194 can be defined by a generally tubular body having a proximal end 194p, a distal end 194*d*, and a central longitudinal axis A5 extending therebetween. The navigation adapter 194 can define a central lumen 196 through which implants or instruments can be inserted. For example, a bone tap or driver instrument for driving a bone screw or other anchor can be inserted through the lumen 196 of the adapter 194. The outer sidewall of the navigation adapter 194 can include one or more longitudinal openings 198.

The navigation adapter 194 can include a protrusion or lug 200. The lug 200 can extend radially-outward from an exterior surface of the adapter 194. The lug 200 can be received within the track 188 of the protection sleeve 184 described above to guide longitudinal movement of the adapter 194 within the protection sleeve and to prevent or limit axial rotation between the adapter and the protection sleeve.

The navigation adapter 194 can include a groove, recess, or other counterpart geometry 202 for mating the navigation adapter to a navigation array (e.g., an array 180 of the type shown in FIG. 5) and/or to an intermediate navigation coupling (e.g., a coupling 182 of the type shown in FIG. 5). Exemplary counterpart geometries that can be included in the navigation adapter 194 are described in U.S. patent application Ser. No. 15/609,712 filed on May 31, 2017 and entitled "COUPLING DEVICES FOR SURGICAL INSTRUMENTS AND RELATED METHODS" which is hereby incorporated by reference herein. As shown for example in FIG. 8D, the point along the length of the navigation adapter 194 at which the navigation array 180 and/or instrument coupling 182 attaches can be distal to the handle portion of an instrument 208 inserted through the navigation adapter. This may be more desirable or ergonomic as compared traditional instruments having a navigation array attached to a proximal end thereof. For example, shifting the weight of the navigation array distally can reduce the lever action applied to the instrument by the weight of the array. As another example, shifting the array distally can provide added clearance for grasping the handle of the instrument 208, or enhanced visibility of the proximal end of the instrument.

The navigation adapter 194 can include a proximal flange, shoulder, or stop 204. The stop 204 can limit distal advancement of the navigation adapter 194 into the protection sleeve 184, e.g., to prevent over-insertion.

The navigation adapter 194 can include features for engaging with an instrument inserted therethrough, e.g., to lock certain types of movement between the adapter and the instrument or to provide drag between the adapter and the instrument. For example, the navigation adapter 194 can include a lock button 206 slidably mounted in a cavity formed in the adapter. The button 206 can be movable along an axis A6 that is perpendicular to the axis A5. The button 206 can include a central opening generally aligned with the lumen 196 of the navigation adapter 194 to allow an instrument inserted through the adapter to pass through the button.

The button 206 can be movable along the axis A6 between a locked position and an unlocked position. In the locked position, a sidewall of the central opening of the button 206 or a protrusion extending therefrom can be positioned within a groove or recess formed in an instrument inserted through the navigation adapter 194. Engagement between the sidewall or protrusion and the groove can limit or prevent longitudinal translation of the instrument relative to the navigation adapter 194 while allowing relative rotation between the instrument and the adapter about the axis A5. In other arrangements, engagement between the sidewall or protrusion and the groove can also limit or prevent rotational movement of the instrument relative to the navigation adapter 194 about the axis A5. In the unlocked position, the sidewall or protrusion of the button opening can be moved out of engagement with the groove formed in the instrument, such that the button 206 does not interfere with rotation or translation of the instrument relative to the navigation adapter 194. The button 206 can be biased towards the locked position, e.g., by a spring. In use, the button 206 can be depressed by a user to allow an instrument to be inserted through the navigation adapter 194. The button 206 can then be released, such that the button springs into engagement with the inserted instrument, e.g., to lock translational movement between the instrument and the navigation adapter 194.

The navigation adapter 194 can include features for providing a friction or drag force between the adapter and an instrument inserted therethrough, e.g., to resist certain movement of the instrument relative to the adapter. For example, the adapter 194 or the instrument can include features for providing resistance to relative rotation between the adapter and the instrument about the axis A5. In one example, the instrument can include a groove with an O-ring disposed therein. The O-ring can drag against the inside diameter of the navigation adapter 194 to provide drag force. In another example, the groove can be formed in the interior of the navigation adapter 194 and the O-ring can be mounted therein to drag against the outside diameter of the instrument. In another example, the instrument can include a plurality of shallow vertical grooves spaced about the outer circumference of the instrument and the navigation adapter 194 can include a spring detent that engages the grooves to click in and out of successive grooves to create drag or resistance as the instrument rotates relative to the adapter. In yet another example, the grooves can be formed in the navigation adapter 194 and the spring detent can be included in the instrument. Multiple of the above drag features can be used in combination. The drag features can be formed in or on or mounted in or on the button 206. The drag features can be formed in or on or mounted in or on the main body of the navigation adapter 194.

Figure 8B:
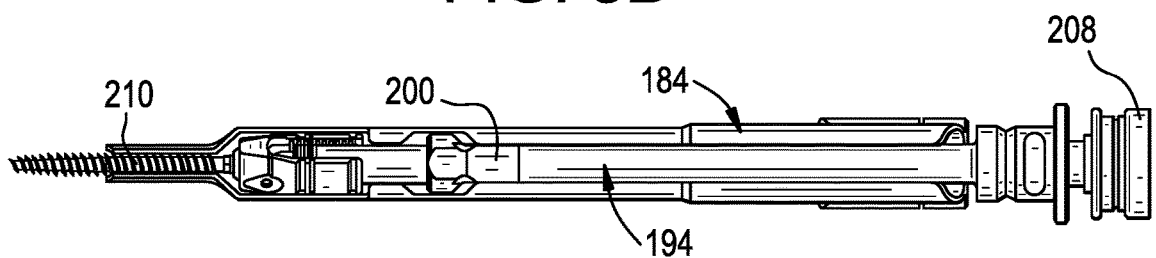
FIG. 8B is a top view of the navigation adapter of FIG. 8A loaded into the protection sleeve of FIG. 6A with a driver instrument and a bone anchor.
Figure 8C:
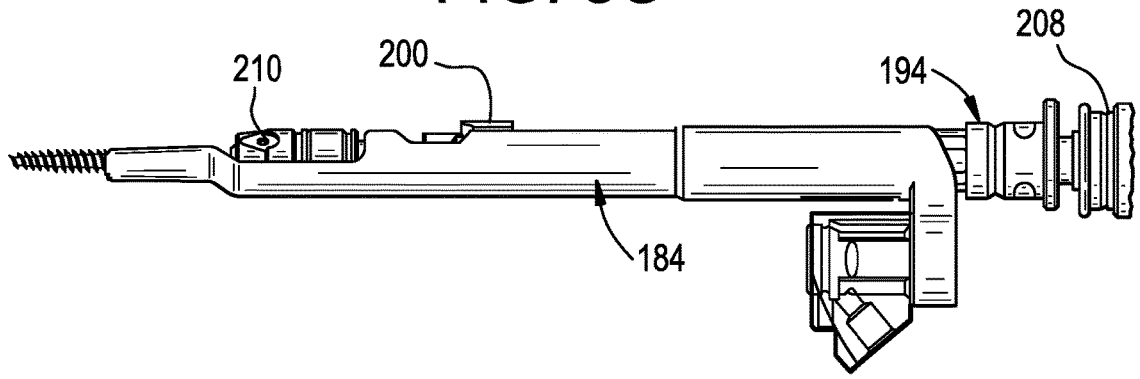
FIG. 8C is a side view of the navigation adapter, protection sleeve, driver instrument, and bone anchor of FIG. 8B.
Figure 8D:
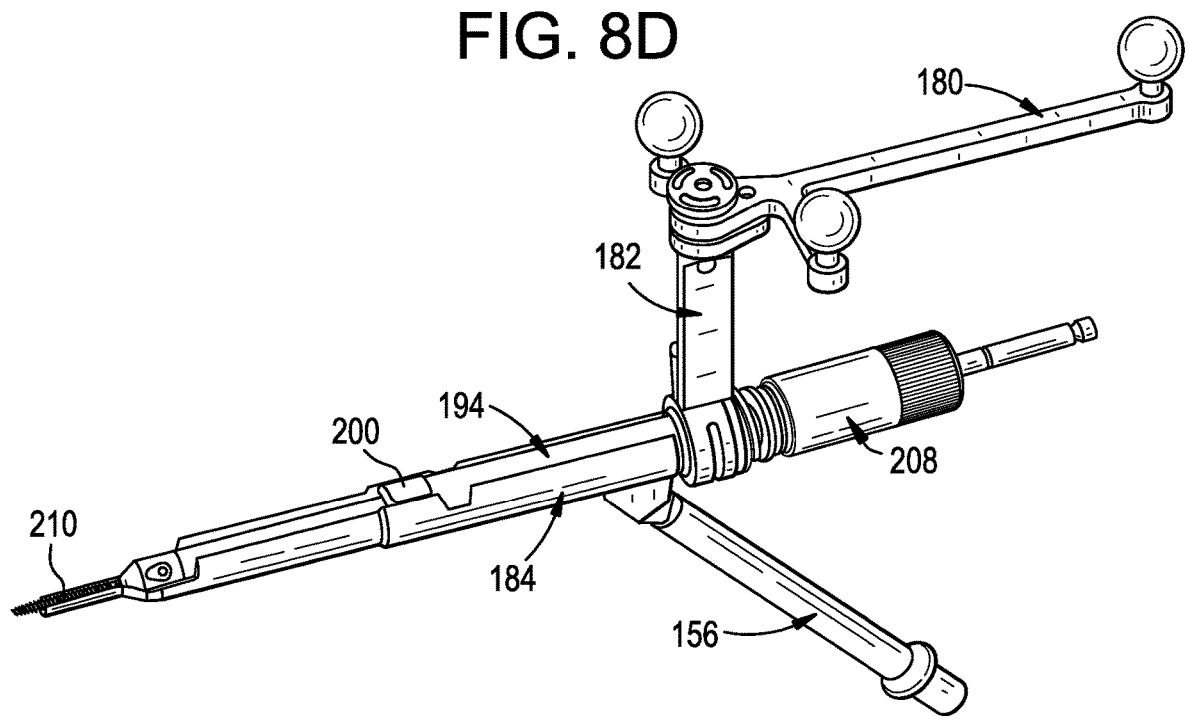
FIG. 8D is a perspective view of the navigation adapter, protection sleeve, driver instrument, and bone anchor of FIG. 8B shown with a navigation array.
Figure 8E:
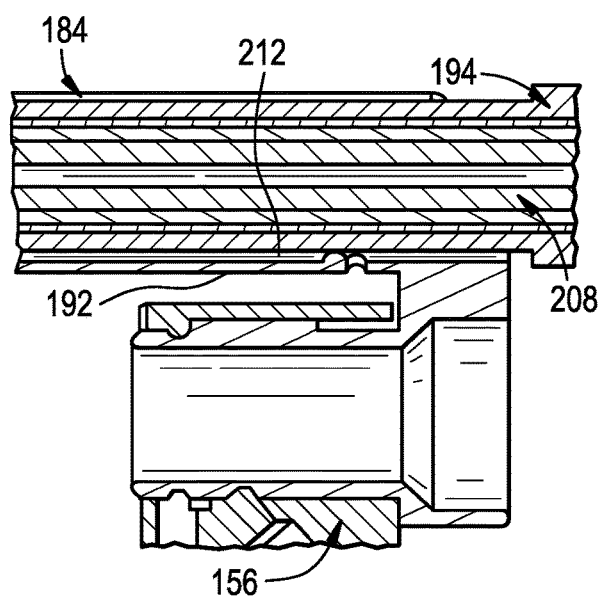
FIG. 8E is a sectional side view of the protection sleeve, navigation adapter, and driver instrument of FIG. 8B.

FIGS. 8B-8D show the navigation adapter 194 inserted through the protection sleeve 184 with a driver instrument 208 and a bone screw or anchor 210 inserted through the navigation adapter. As shown in FIG. 8E, the navigation adapter 194 can have a reduced diameter or longitudinal groove 212 that receives the spring tab 192 of the protection sleeve 184, such that the spring tab does not lock longitudinal translation between the navigation adapter and the protection sleeve. Accordingly, the navigation adapter 194 can translate longitudinally, e.g., during bone anchor driving, relative to the protection sleeve 184.

The navigation adapter 194 does not necessarily need to be used in conjunction with the protection sleeve 184. Rather, as shown in FIG. 8F, the navigation adapter 194 can be used without the protection sleeve 184, e.g., to guide a driver instrument 208 and bone anchor 210 as shown.

Figure 8G:
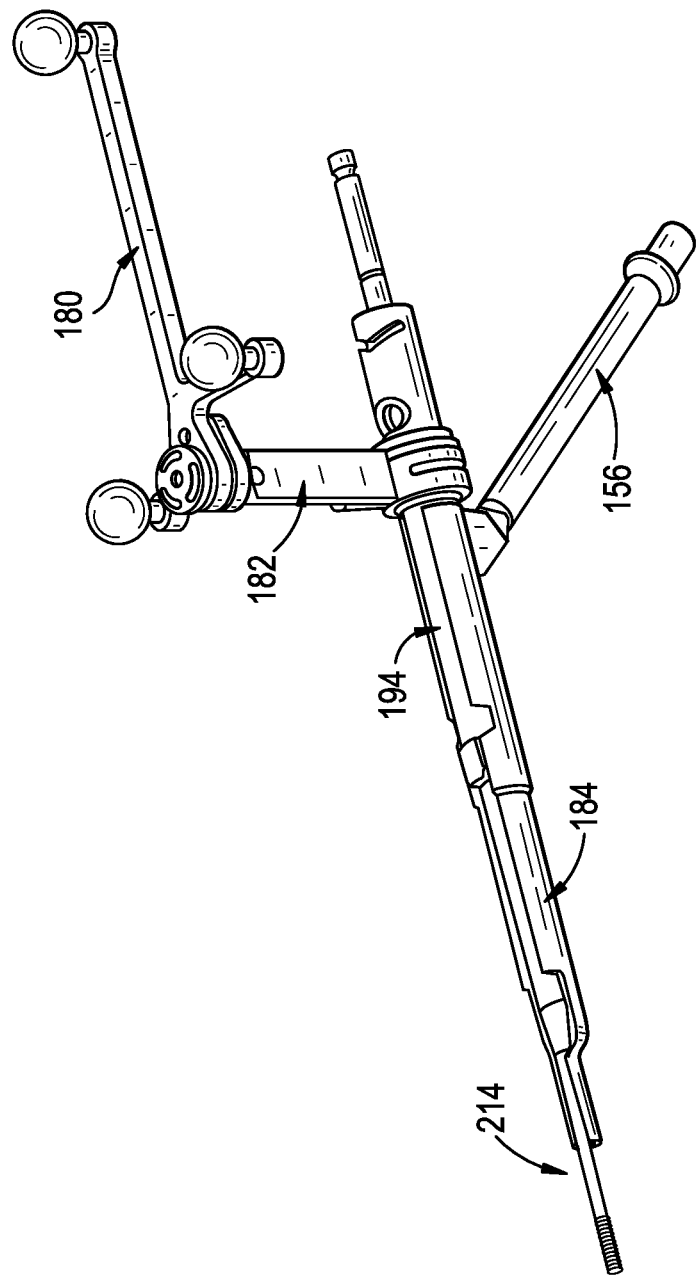
FIG. 8G is a perspective view of the navigation adapter of FIG. 8A loaded into the protection sleeve of FIG. 6A with a bone tap instrument.
Figure 8H:
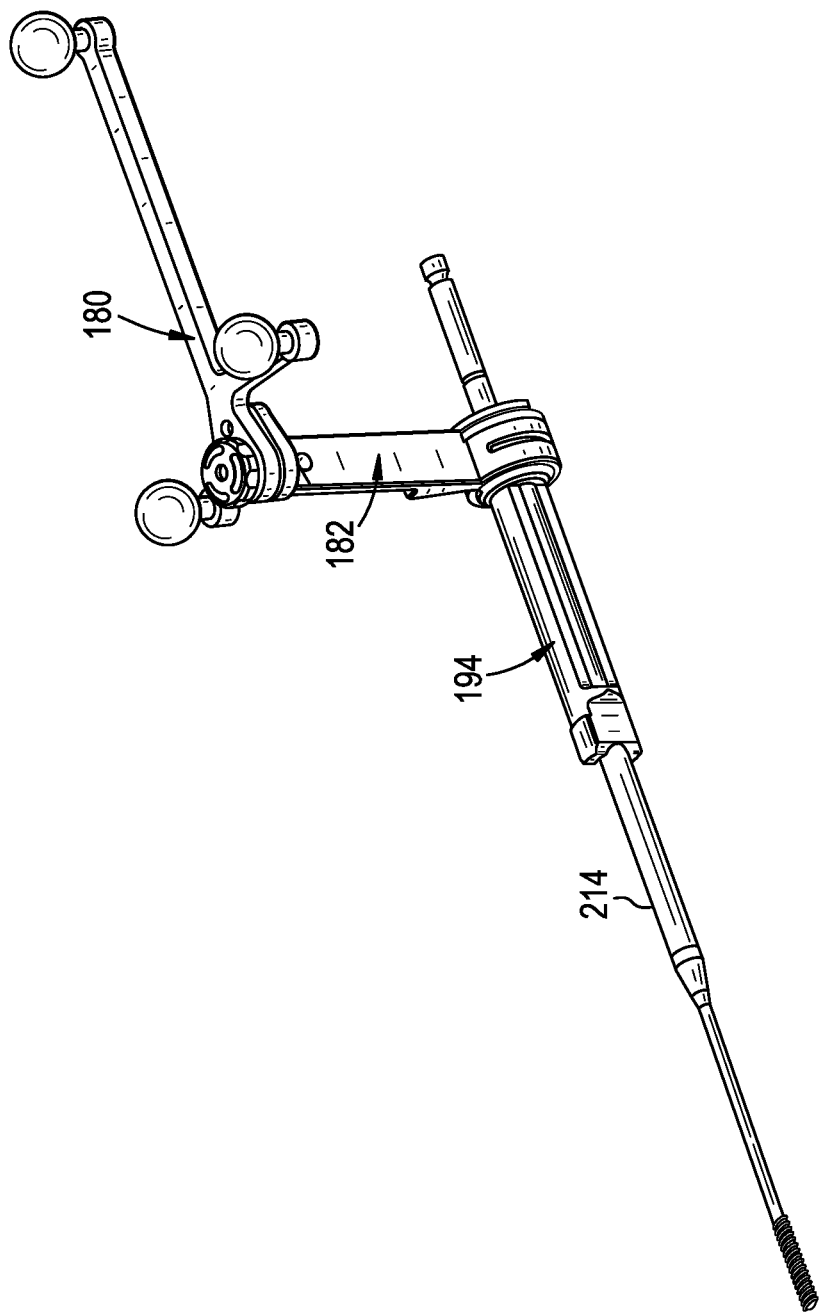
FIG. 8H is a perspective view of the navigation adapter of FIG. 8A guiding a bone tap instrument without use of a protection sleeve.

The navigation adapter 194 can be used with a bone tap 214. FIG. 8G illustrates the navigation adapter 194 guiding a bone tap 214 within the protection sleeve 184. FIG. 8H illustrates the navigation adapter 194 guiding a bone tap 214 without the protection sleeve 184.

An exemplary surgical method of using the drill guides and accessories above to implant a bone anchor is as follows. The drill guide 100 can be positioned with a distal tip of the body 104 in contact with a desired bone entry point and with the axis A1 of the guide aligned with the desired bone anchor trajectory. The drill guide 100 can be so positioned in a free-hand manner, with the aid of fluoroscopy or other imaging technology, and/or informed by a surgical navigation system, e.g., using a navigation array 180 and/or instrument coupling 182 mated to the drill guide. The drill guide 100 can be positioned in such a way while disposed through a protection sleeve 184, for example when implanting a bone anchor in a C1 vertebra of a patient. Before or after positioning the drill guide 100, the depth setting of the drill guide can be adjusted to achieve the desired drilling depth into the bone. With the entry point and trajectory established, and the desired depth setting selected, a drill can be advanced through the drill guide 100 to drill a pilot hole in the bone. The drill and drill guide 100 can then be removed, leaving the protection sleeve 184 in place if applicable. The drill and drill guide 100 can be replaced with the navigation adapter 194. A bone tap 214 can be inserted through the navigation adapter 194 and guided into the previously-formed hole, e.g., using a navigation array 180 and/or instrument coupling 182 attached to the navigation adapter. The bone tap 214 can be removed from the navigation adapter 194 and replaced with a bone anchor 210 and an anchor driver 208. The bone anchor 210 can then be driven into the bone, with the navigation adapter 194 providing navigated bone anchor advancement. Accordingly, the drill guide and accessories described above can provide a simple and intuitive system for navigated drilling, tapping, and/or driving of a bone anchor.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. An adjustable length guide device, comprising:
a body having a proximal end, a distal end, and a central longitudinal axis extending between the proximal and distal ends;
a stem movably coupled to the body, the body and the stem together defining an adjustable length guide lumen; and
an adjustment mechanism that controls movement of the stem relative to the body to incrementally adjust the length of the guide lumen;
wherein the adjustment mechanism comprises a knob having at least one pin received within a groove formed in an outer surface of the body;
wherein the at least one pin is positionable in: (i) a locking region of the groove to prevent adjustment of the length of the guide lumen; and (ii) an adjustment region of the groove to allow adjustment of the length of the guide lumen, and
wherein a central longitudinal axis of the knob is coaxial with a central longitudinal axis of one or more of the stem and the body.

2. The device of claim 1, wherein:
positioning the at least one pin in the locking region of the groove prevents the knob and the stem from rotating relative to body about the central longitudinal axis while allowing the knob to translate longitudinally relative to body; and
positioning the at least one pin in the adjustment region of the groove allows the knob and the stem to rotate relative to the body about the central longitudinal axis.

3. The device of claim 1, wherein the stem is threadably engaged with the body and wherein the knob is rotationally fixed relative to the stem such that rotation of the knob relative to the body adjusts the length of the guide lumen.

4. The device of claim 1, wherein the knob is movable relative to the body in an adjustment cycle in which the knob (i) translates distally relative to the body by a first distance, (ii) rotates relative to the body by a first rotational amount, and (iii) returns proximally relative to the body by the first distance, the adjustment cycle being effective to adjust the length of the guide lumen by one increment.

5. The device of claim 4, wherein the adjustment cycle comprises moving the at least one pin out of the locking region of the groove, along the adjustment region of the groove, and back into the locking region of the groove.

6. The device of claim 4, wherein the first rotational amount is less than 360 degrees.

7. The device of claim 4, wherein the first rotational amount is 180 degrees.

8. The device of claim 4, wherein rotating the knob relative to the body by the first rotational amount translates the knob distally relative to the body by a second amount and returns the knob proximally relative to the body by the second amount.

9. The device of claim 1, wherein the locking region of the groove comprises first and second diametrically opposed longitudinal sections of the groove oriented parallel to the longitudinal axis of the body.

10. The device of claim 9, wherein the adjustment region of the groove comprises first and second diametrically opposed circumferential sections of the groove connecting the first and second longitudinal sections.

11. The device of claim 10, wherein each of the circumferential sections is chevron-shaped.

12. The device of claim 10, wherein each of the circumferential sections comprises a quarter turn helical down thread and a quarter turn helical up thread.

13. The device of claim 1, wherein the knob is biased proximally relative to the body to urge the at least one pin towards the locking region of the groove.

14. The device of claim 1, further comprising a handle selectively attachable to the body.

15. The device of claim 14, wherein the handle comprises an inner locking shaft rotatable relative to an outer shaft of the handle between a locked position, in which a distal tip of the locking shaft engages the body to lock the handle to the body, and an unlocked position in which the distal tip of the locking shaft does not engage the body.

16. The device of claim 15, wherein the distal tip comprises a slash-cut portion that is aligned with a groove in the body in the unlocked position and a non-cut portion that is disposed in the groove in the body in the locked position.

17. The device of claim 1, wherein the knob circumferentially surrounds the stem.

18. The device of claim 1, wherein the knob is non-rotatably coupled to the stem and free to translate relative thereto.

19. An adjustable length guide device, comprising:
a body having a proximal end, a distal end, and a central longitudinal axis extending between the proximal and distal ends;
a stem movably coupled to the body, the body and the stem together defining an adjustable length guide lumen; and
an adjustment mechanism that controls movement of the stem relative to the body to incrementally adjust the length of the guide lumen;
wherein the adjustment mechanism comprises a knob having at least one pin received within a groove formed in an outer surface of the body;
wherein the at least one pin is positionable in: (i) a locking region of the groove to prevent adjustment of the length of the guide lumen; and (ii) an adjustment region of the groove to allow adjustment of the length of the guide lumen, and
wherein the knob receives at least a portion of the stem therethrough.

20. An adjustable length guide device, comprising:
a body having a proximal end, a distal end, and a central longitudinal axis extending between the proximal and distal ends;
a stem movably coupled to the body, the body and the stem together defining an adjustable length guide lumen; and
an adjustment mechanism that controls movement of the stem relative to the body to incrementally adjust the length of the guide lumen;
wherein the adjustment mechanism comprises a knob having at least one pin received within a groove formed in an outer surface of the body;
wherein the at least one pin is positionable in: (i) a locking region of the groove to prevent adjustment of the length of the guide lumen; and (ii) an adjustment region of the groove to allow adjustment of the length of the guide lumen, and
wherein the knob is configured to translate relative to the stem along a longitudinal axis thereof.

* * * * *